United States Patent [19]

Cushman et al.

[11] Patent Number: 5,439,899
[45] Date of Patent: Aug. 8, 1995

[54] COSALANE AND RELATED COMPOUNDS HAVING ACTIVITY AGAINST AIDS AND AIDS-RELATED INFECTIONS

[75] Inventors: Mark Cushman, West Lafayette, Ind.; Rudiger D. Haugwitz, Bethesda, Md.; Wieslaw M. Golebiewski, West Lafayette, Ind.

[73] Assignees: Purdue Research Foundation, West Lafayette, Ind.; The United States of America as represented by the Department of Health and Human Services, Washington, D.C.

[21] Appl. No.: 29,415

[22] Filed: Mar. 10, 1993

[51] Int. Cl.$^6$ ............................................. C07J 9/00
[52] U.S. Cl. ................................. 514/169; 514/182; 552/540; 552/506; 552/522; 552/525
[58] Field of Search ............ 552/540, 522, 525, 506; 514/169, 171, 182

[56] References Cited

U.S. PATENT DOCUMENTS

| | | | |
|---|---|---|---|
| 2,592,036 | 4/1952 | Kaiser et al. | 260/397.1 |
| 3,684,801 | 8/1972 | Breslow et al. | 260/239.57 |
| 4,343,796 | 8/1982 | Groen | 424/184 |
| 4,395,408 | 7/1983 | Torelli et al. | 424/238 |
| 4,434,218 | 1/1984 | Deraedt et al. | 424/238 |
| 4,942,154 | 7/1990 | Durette et al. | 514/26 |
| 4,956,355 | 9/1990 | Prendergast | 514/178 |
| 4,970,199 | 11/1990 | Durette et al. | 514/26 |
| 4,970,212 | 11/1990 | Nowicky | 514/279 |
| 5,039,688 | 8/1991 | Lewis | 514/358 |
| 5,077,284 | 12/1991 | Loria et al. | 514/171 |

OTHER PUBLICATIONS

Cushman et al., "Inhibition of HIV-1 Integration Protein By Aurintricarboxylic Acid Monomers, Monomer Analogs, and Polymer Fractions", *Biochemical and Biophysical Research Communications*, 185(1):85–90 (1992).

Cushman et al., "Structural Investigation and Anti--HIV Activities of High Molecular Weight ATA Polymers", *J. Org. Chem.*, 57:7241–7248 (1992).

Wang et al., "Isolation and Structure Elucidation of Low Molecular Weight Components of Aurintricarboxylic Acid (ATA)", *J. Org. Chem.*, 57:3861–3866 (1992).

Cushman et al., "Preparation and Anti-HIV Activities of Aurintricarboxylic Acid Fractions and Analogues: Direct Correlation of Antiviral Potency with Molecular Weight", *J. Med. Chem.*, 1991, 34:329–337 (1991).

Weislow et al., "New Soluble-Formazan Assay for HIV-1 Cytopathic Effects: Application to High-Flux Screening of Synthetic and Natural Products for AIDS-Antiviral Activity", *Journal of the National Cancer Institute*, 81(8):577–86, Apr. 19, 1989.

Cushman et al., "Synthesis and Anti-HIV Activities of Low Molecular Weight Aurintricarboxylic Acid Fragments and Related Compounds", *J. of Med. Chem.*, 34:337–342 (1991).

Buckheit et al., "Characterization of an HIV-1 Isolate Displaying an Apparent Absence of Virion-Associated Reverse Transcriptase Activity", *AIDS Research and Human Retroviruses*, 7(3):295–302 (1991).

Hoffman et al., "Characterization of the AIDS-Associated Retrovirus Reverse Transcriptase and Optimal Conditions for Its Detection in Virions", *Virology*, 147:326–335 (1985).

Cushman et al., "Synthesis of the Covalent Hydrate of the Incorrectly Assumed Structure of Aurintricarboxylic Acid (ATA)", *Tetrahedron*, 46(5):1491–1498 (1990).

Bose et al., "Transformations of Seroid Ketones Using Phosphonate Carbanions", *Transformations of Steroid Ketones*, 30:505–509, Feb. 1965.

*Primary Examiner*—Johann Richter
*Assistant Examiner*—Rebecca Cook
*Attorney, Agent, or Firm*—Leydig, Voit & Mayer Ltd.

[57] ABSTRACT

Novel compounds having anti-HIV activity are disclosed along with formulations and methods for treating human immunodeficiency viral infections employing these compounds.

9 Claims, 3 Drawing Sheets

COSALANE AND RELATED COMPOUNDS HAVING ACTIVITY AGAINST AIDS AND AIDS-RELATED INFECTIONS

This invention was made with government support under Grant #N01-CM-17513. The government has certain rights to this invention.

TECHNICAL FIELD OF THE INVENTION

The present invention is directed, in general, to methods for treating AIDS and AIDS-related infections and in particular to new compounds having anti-HIV activity, to pharmaceutical formulations containing such compounds, and to methods for the treatment of infections caused by a human immunodeficiency virus, such as HIV.

BACKGROUND OF THE INVENTION

Only a decade ago, AIDS was virtually unknown. This puzzling affliction was seen only in a small number of homosexual men. However, today it is difficult to find anyone who has not heard of AIDS, the disease that can debilitate and then kill its victim.

Acquired immune deficiency syndrome (AIDS) is a fatal disease, reported cases of which have increased dramatically within the past several years. Estimates of reported cases also continue to rise dramatically. Consequently, there is a great need to develop drugs and vaccines to combat AIDS.

The AIDS virus was first identified in 1983. It has been known by several names and acronyms. It is the third known T-lymphocyte virus (HTLV-III), and it has the capacity to replicate within cells of the immune system, causing profound cell destruction. The AIDS virus is a retrovirus, a virus that uses reverse transcriptase during replication. This particular retrovirus is also known as lymphadenopathy-associated virus (LAV), AIDS-related virus (ARV) and, most recently, as human immunodeficiency virus (HIV). Two distinct families of HIV have been described to date, namely HIV-1 and HIV-2. The acronym HIV will be used herein to refer to HIV viruses generically.

Specifically, HIV is known to exert a profound cytopathic effect on the CD4+ helper/inducer T-cells, thereby severely compromising the immune system. HIV infection also results in neurological deterioration and, ultimately, in the death of the infected individual.

Thus far, there is no cure for AIDS.

The field of viral chemotherapeutics has developed in response to the need for agents effective against retroviruses, in particular HIV. There are many ways in which an agent can exhibit anti-retroviral activity. For example, HIV requires at least four viral proteins for replication: reverse transcriptase (RT), protease (PR), transactivator protein (TAT), and regulator of virion-protein expression (REV). Accordingly, viral replication could theoretically be inhibited through inhibition of any one or all of the proteins involved in viral replication. Anti-retroviral agents, such as AZT and ddC, are known to inhibit RT. There also exist anti-retroviral agents that inhibit TAT.

Nucleoside derivatives, such as AZT, are the only clinically active agents that are currently available for antiviral therapy. Although very useful, the utility of AZT and related compounds is limited by toxicity and insufficient therapeutic indices for fully adequate therapy. The development of AZT-resistant strains of HIV also limits the utility of AZT in the treatment of AIDS.

Synthetic peptides also are being developed for potential use as inhibitors of the retroviral PR in the treatment of AIDS. Although these inhibitors are effective in preventing the retroviral PR from functioning, the inhibitors suffer from some distinct disadvantages. First, since the active site of the PR is hindered, i.e., has reduced accessibility as compared to the remainder of the PR, the ability of the inhibitors to access and bind in the active site of the PR is impaired. Secondly, the peptide inhibitors that bind to the active site of the PR are generally poorly soluble in water, causing distinct problems in drug delivery.

Therefore, new classes of anti-retroviral agents to be used alone or in combination with AZT and/or other agents are urgently needed for effective anti-retroviral therapy against HIV. New agents which may be used to prevent HIV infection are also important.

SUMMARY OF THE INVENTION

In accordance with the present invention, it has now been discovered that certain compounds, as defined in Formulas I, II, and III below, are capable of preventing the replication of a retrovirus in a cell, such as a human T cell, infected with such a retrovirus. Also, infections of animals, particularly humans, by a human immunodeficiency virus, may be effectively treated with certain compounds, as defined in Formulas I, II and III.

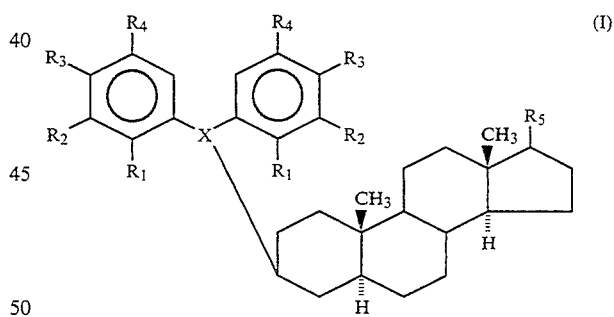

(I)

wherein $R_1$ to $R_5$ independently are H, a halogen, hydroxy, amino, lower alkoxy, benzoyloxy, or lower acyloxy, COOH or a salt thereof, $SO_3H$ or a salt thereof, $PO_3H_2$ or a salt thereof, $C_8H_{17}$ or a longer chain alkyl, or aryl group, COOR where R is aryl or lower alkyl, $SO_3R$ where R is aryl or lower alkyl, $PO_3(R)_2$ where R is aryl or lower alkyl, CONR'R" where R' and R" are each independently H, lower alkyl, aryl, or OH, $SO_2NR'R"$ where R' and R" are each independently H, lower alkyl, or aryl, SR where R is lower alkyl or aryl, $SCH_2Ph$, SCOR where R is lower alkyl or aryl, NR'R" where R' and R" are each independently H, lower alkyl, or aryl; and X is an alkane or alkene radical having one to seven carbon atoms.

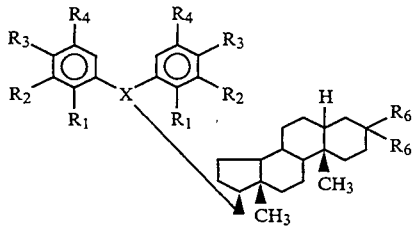
(II)

wherein $R_1$ to $R_5$ independently are H, a halogen, hydroxy, amino, lower alkoxy, benzoyloxy, or lower acyloxy, COOH or a salt thereof, $SO_3H$ or a salt thereof, $PO_3H_2$ or a salt thereof, $C_8H_{17}$ or a longer chain alkyl, or aryl group, COOR where R is aryl or lower alkyl, $SO_3R$ where R is aryl or lower alkyl, $PO_3(R)_2$ where R is aryl or lower alkyl, CONR'R" where R' and R" are each independently H, lower alkyl, aryl, or OH, $SO_2NR'R''$ where R' and R" are each independently H, lower alkyl, or aryl, SR where R is lower alkyl or aryl, $SCH_2Ph$, SCOR where R is lower alkyl or aryl, NR'R" where R' and R" are each independently H lower alkyl, or aryl; and X is an alkane or alkene radical having one to seven carbon atoms.

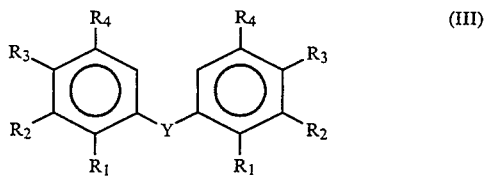
(III)

wherein $R_1$ to $R_5$ independently are H, a halogen, hydroxy, amino, lower alkoxy, benzoyloxy, or lower acyloxy, COOH or a salt thereof, $SO_3H$ or a salt thereof, $PO_3H_2$ or a salt thereof, $C_8H_{17}$ or a longer chain alkyl, or aryl group, COOR where R is aryl or lower alkyl, $SO_3R$ where R is aryl or lower alkyl, $PO_3(R)_2$ where R is aryl or lower alkyl, CONR'R" where R' and R" are each independently H, lower alkyl, aryl, or OH, $SO_2NR'R''$ where R' and R" are each independently H, lower alkyl, or aryl, SR where R is lower alkyl or aryl, $SCH_2Ph$, SCOR where R is lower alkyl or aryl, NR'R" where R' and R" are each independently H, lower alkyl, or aryl; and Y is an alkane radical having one to seventeen carbon atoms, or an alkene radical having one to thirty-one carbon atoms which may be substituted with Br, pentafluorophenyl, or adamantane.

The present invention also provides for a method of inhibiting retroviral replication of a retrovirus, particularly a human immunodeficiency virus, specifically HIV-1 or HIV-2, in a mammalian cell, particularly a human cell, with an effective amount of a compound defined in Formulas I, II, or III.

Also provided is a method of treating an animal, particularly, a human, infected with a human immunodeficiency virus, comprising administering a quantity of a compound as defined in Formulas I, II or III, sufficient to be pharmacologically effective in treating such an infection, in particular one caused by HIV-1 or HIV-2. Also provided is a method of preventing an animal, particularly, a human, from being infected with a human immunodeficiency virus, comprising administering a quantity of a compound as defined in Formulas I, II or III, sufficient to be prophylactically effective in preventing such an infection, in particular one caused by HIV-1 or HIV-2. The compound may be administered in any suitable manner, including orally, buccally, sublingually, subcutaneously, intramuscularly, intravenously or rectally.

Further provided are the aforementioned compounds as formulations for administration to patients for the treatment of, and prophylaxis against, a human immunodeficiency syndrome, specifically AIDS and AIDS-related infections. Thus, there is also provided a pharmaceutical composition of matter comprising a compound of Formula I, II or III or a pharmaceutically acceptable carrier therefor. Additionally, the present invention provides for a pharmaceutical composition of matter, in unit dosage form, for use as an anti-HIV agent, said composition comprising (i) a pharmacologically effective amount of a compound of Formula I, II or III; and (ii) a pharmaceutically acceptable carrier therefor. The quantity of active agent that is administered will vary widely. For example, the amount may be from about 0.01 to 5 mg per kg of body weight administered 1 to 5 times per day.

Other advantages of the invention will become apparent from the following description herein.

DETAILED DESCRIPTION OF THE INVENTION

Figure 1:
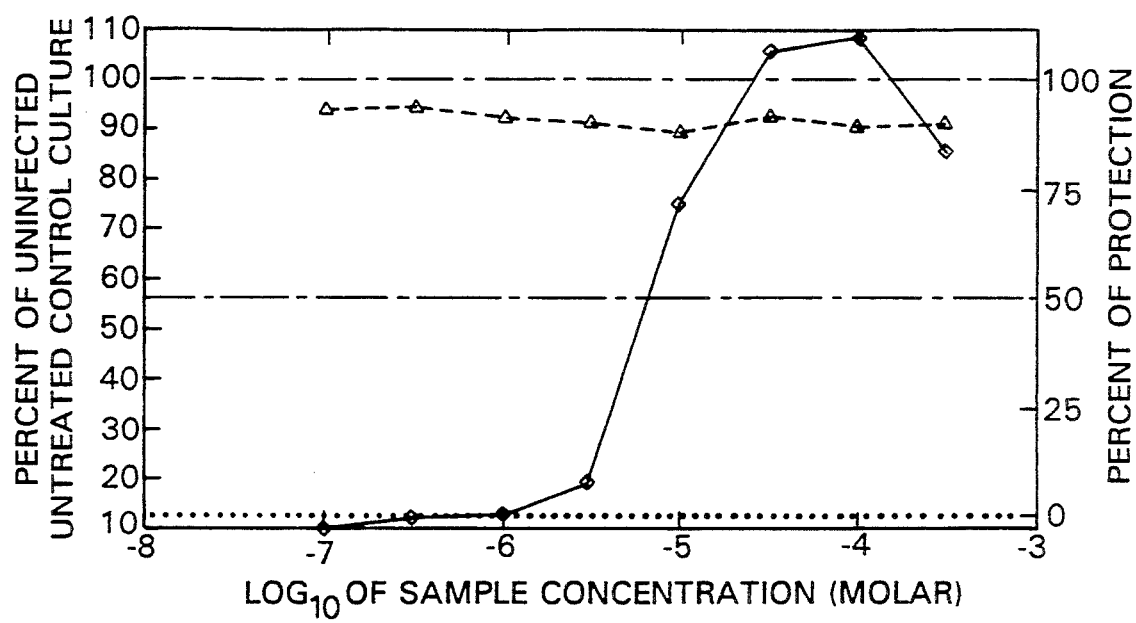
FIG. 1 depicts in vitro testing results for anti-HIV activity for the compound of Example 1 in accordance with the present invention.
Figure 2:
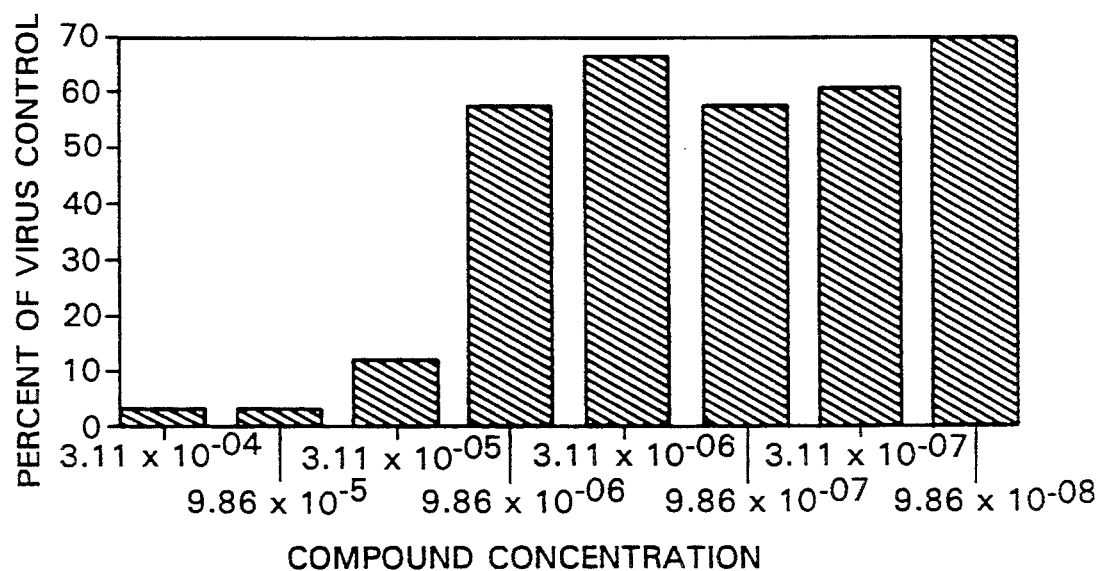
FIG. 2 depicts in vitro testing results for infectious particles thereby indicating anti-HIV activity for the compound of Example 1 in accordance with the present invention.
Figure 3:
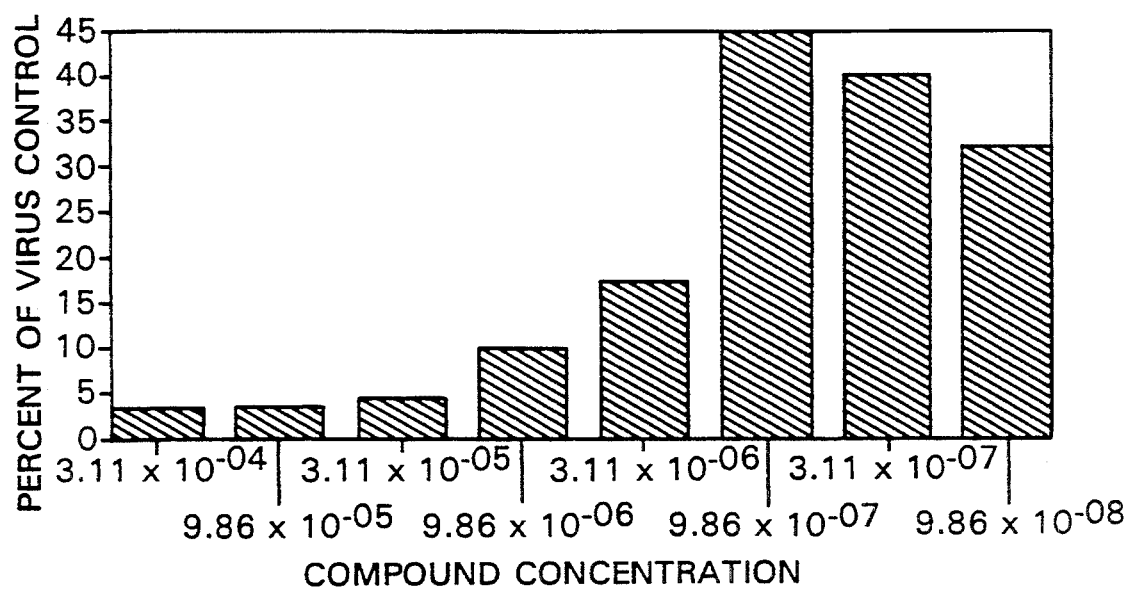
FIG. 3 depicts in vitro testing results for p24 thereby indicating anti-HIV activity for the compound of Example 1 in accordance with the present invention.
Figure 4:
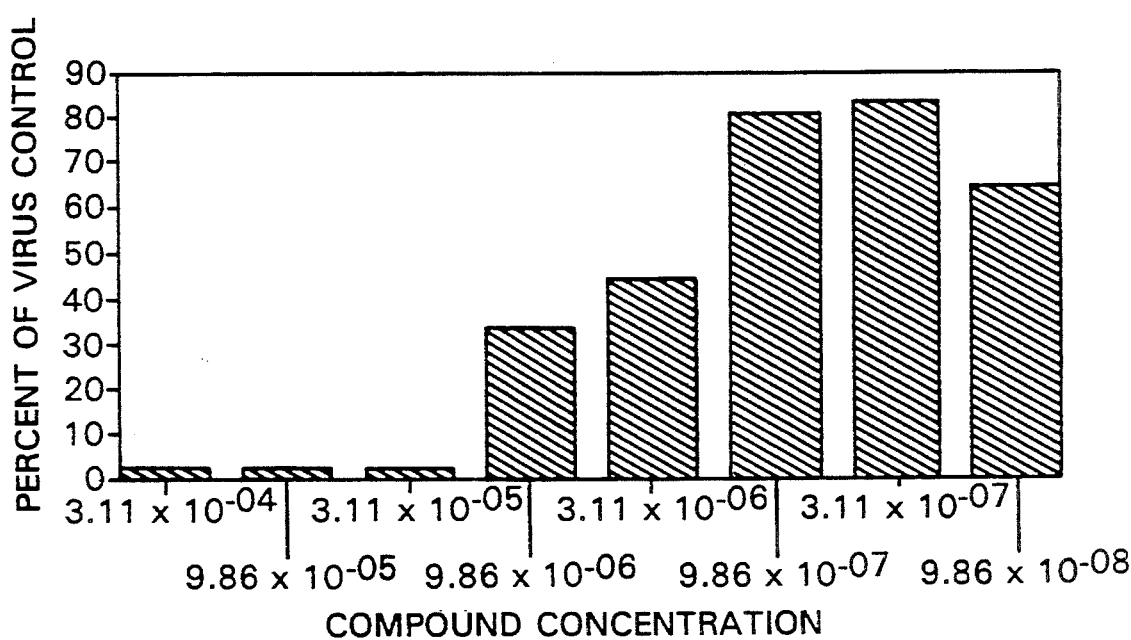
FIG. 4 depicts in vitro testing results for reverse transcriptase activity thereby indicating anti-HIV activity for the compound of Example 1 in accordance with the present invention.

Compounds of the present invention are described by the general Formulas I, II and III:

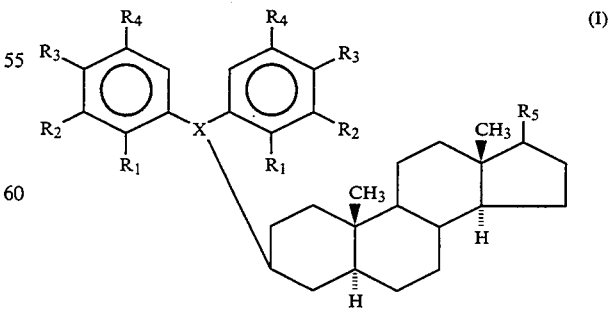
(I)

wherein $R_1$ to $R_5$ independently are H, a halogen, hydroxy, amino, lower alkoxy, benzoyloxy, or lower acyloxy, COOH or a salt thereof, $SO_3H$ or a salt thereof, $PO_3H_2$ or a salt thereof, $C_8H_{17}$ or a longer chain alkyl, or aryl group, COOR where R is aryl or lower alkyl, $SO_3R$ where R is aryl or lower alkyl, $PO_3(R)_2$ where R is aryl or lower alkyl, CONR'R" where R' and R" are each independently H, lower alkyl, aryl, or OH, $SO_2NR'R"$ where R' and R" are each independently H, lower alkyl, or aryl, SR where R is lower alkyl or aryl, $SCH_2Ph$, SCOR where R is lower alkyl or aryl, NR'R" where R' and R" are each independently H, lower alkyl, or aryl; and X is an alkane or alkene radical having one to seven carbon atoms.

A compound defined generally by Formula I and specifically by structure IV has been named cosalane and has been found to be a highly effective anti-HIV agent in vitro. Cosalane is a stable, colorless powder, mp 200° C. It is soluble in ethanol, methanol, DMSO, and water; $^1H$ NMR ($CD_3OD$, 500 MHz) $\delta$5.95 (t, J=7 Hz, 1H), 0.91 (d, J=6.5 Hz, 3H), 0.88 (dd, J-6.5 Hz), 0.73 (s, 3H), 0.66 (s, 3H); IR (KBr) 3181. 2926, 2852, 1656, 1462, 1376, 1261, 1183, 1101 $cm^{-1}$.

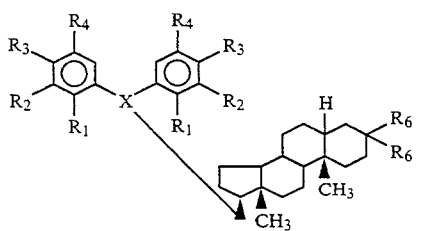
(II)

wherein $R_1$ to $R_5$ independently are H, a halogen, hydroxy, amino, lower alkoxy, benzoyloxy, or lower acyloxy, COOH or a salt thereof, $SO_3H$ or a salt thereof, $PO_3H_2$ or a salt thereof, $C_8H_{17}$ or a longer chain alkyl, or aryl group, COOR where R is aryl or lower alkyl, $SO_3R$ where R is aryl or lower alkyl, $PO_3(R)_2$ where R is aryl or lower alkyl, CONR'R" where R' and R" are each independently H, lower alkyl, aryl, or OH, $SO_2NR'R"$ where R' and R" are each independently H, lower alkyl, or aryl, SR where R is lower alkyl or aryl, $SCH_2Ph$, SCOR where R is lower alkyl or aryl, NR'R" where R' and R" are each independently H, lower alkyl, or aryl; and X is an alkane or alkene radical having one to seven carbon atoms.

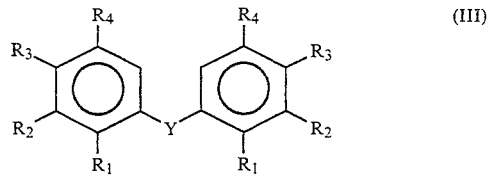
(III)

wherein $R_1$ to $R_5$ independently are H, a halogen, hydroxy, amino, lower alkoxy, benzoyloxy, or lower acyloxy, COOH or a salt thereof, $SO_3H$ a salt thereof, $PO_3H_2$ or a salt thereof, $C_8H_{17}$ or a longer chain alkyl, or aryl group, COOR where R is aryl or lower alkyl, $SO_3R$ where R is aryl or lower alkyl, $PO_3(R)_2$ where R is aryl or lower alkyl, CONR'R" where R' and R" are each independently H, lower alkyl, aryl, or OH, $SO_2NR'R"$ where R' and R" are each independently H, lower alkyl, or aryl, SR where R is lower alkyl or aryl, $SCH_2Ph$, SCOR where R is lower alkyl or aryl, NR'R" where R' and R" are each independently H, lower alkyl, or aryl; and Y is an alkane radical having one to seventeen carbon atoms, or an alkene radical having one to thirty-one carbon atoms which may be substituted with Br, pentafluorophenyl, or adamantane.

By the term lower alkyl in the definition of Formulas I, II, and III, we mean an alkyl group having 1 to 5 carbon atoms.

By longer chain alkyl group, we mean an alkyl group having 8 to 24 carbon atoms.

By lower alkoxy and lower acyloxy, we mean alkoxy or acyloxy groups having 1 to 5 carbon atoms.

Preferably, the novel compounds have the structures indicated by Formulas IV–XXVII.

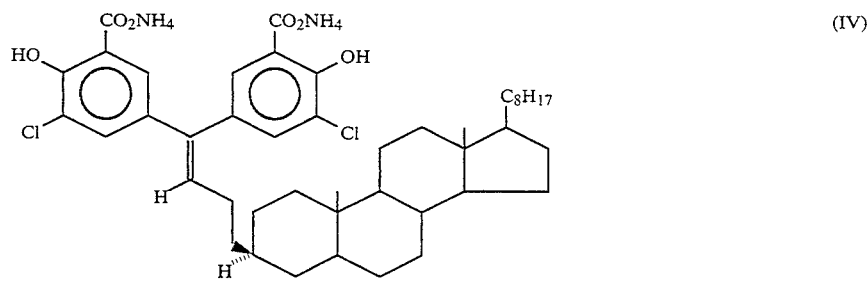
(IV)

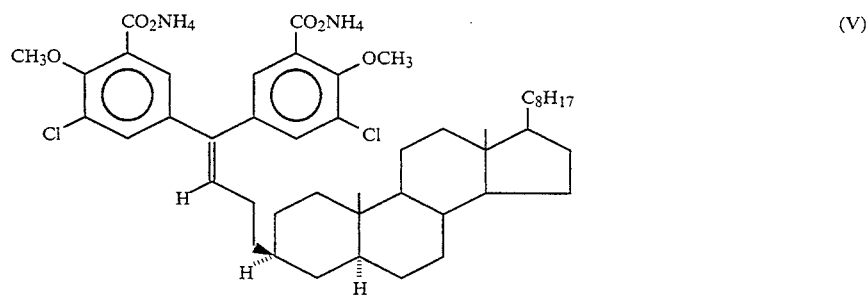
(V)

-continued
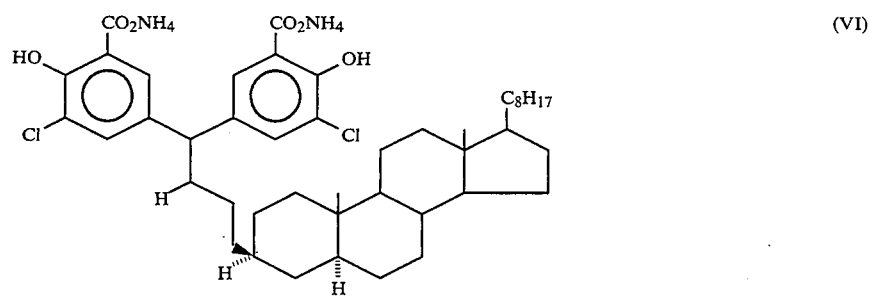
(VI)
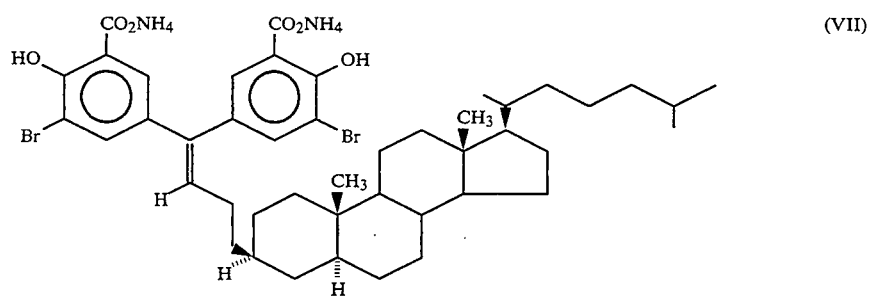
(VII)
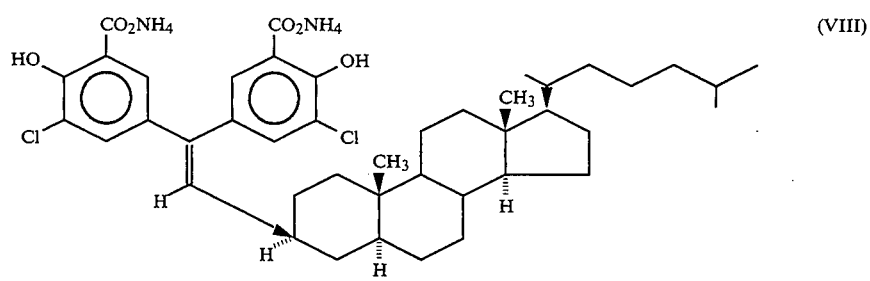
(VIII)
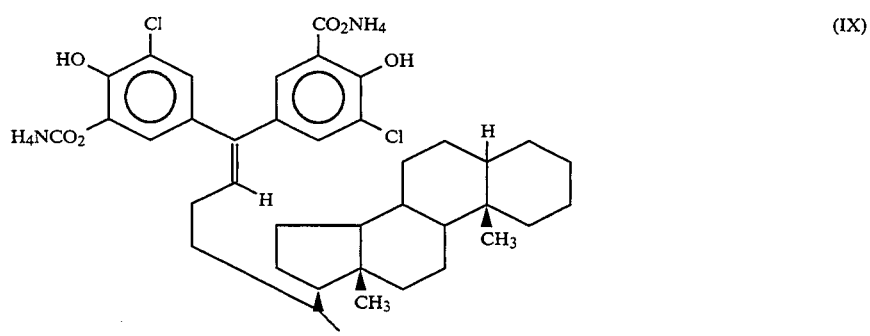
(IX)
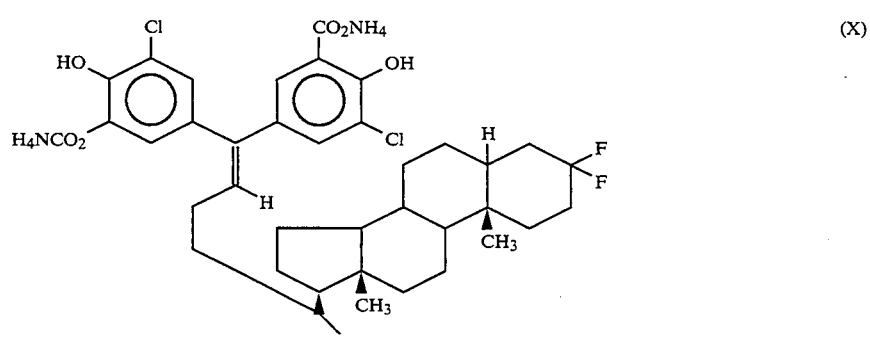
(X)

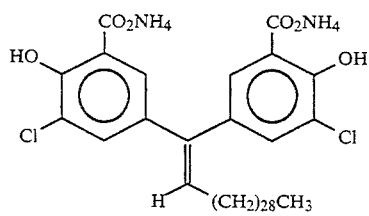
(XI)
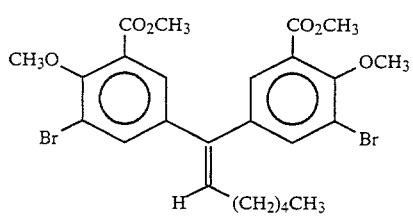
(XII)
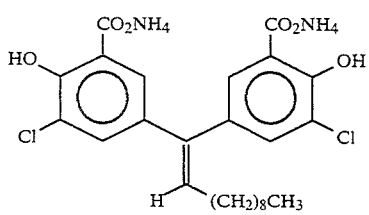
(XIII)
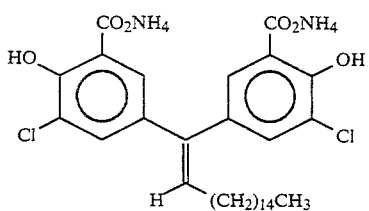
(XIV)
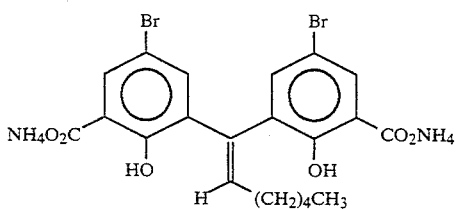
(XV)
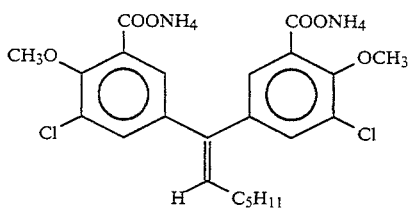
(XVI)
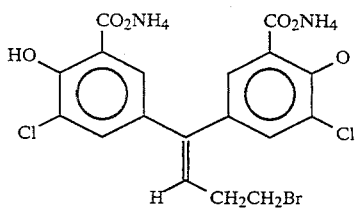
(XVII)
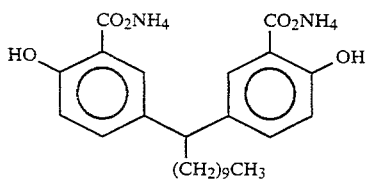
(XVIII)

-continued
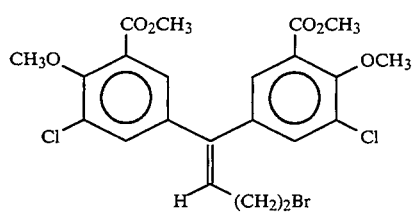
(XIX)
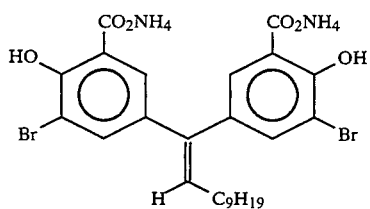
(XX)
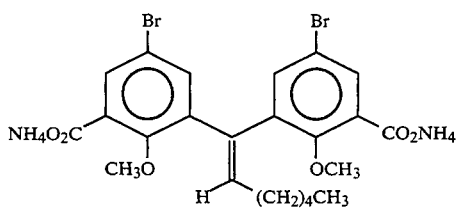
(XXI)
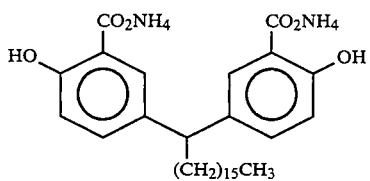
(XXII)
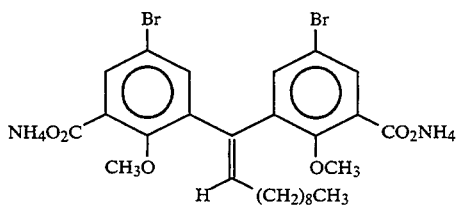
(XXIII)
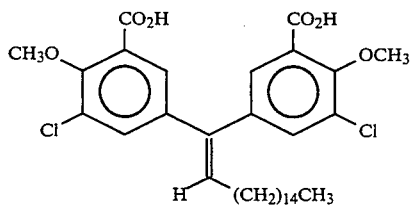
(XXIV)
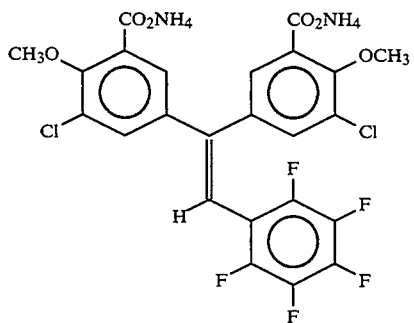
(XXV)

(XXVI)

[Structure: bis(methyl 3-chloro-4-methoxybenzoate) vinyl with (CH2)4CH3]

(XXVII)

[Structure: bis(ammonium 3-chloro-4-methoxybenzoate) vinyl with (CH2)8CH3]

As disclosed in U.S. Pat. Nos. 4,970,199 and 4,942,154, certain steroidal compounds having a basic steroidal ring structure as in the compounds of the present invention (steroidal derivatives of glycolipids), are known to possess activity as host resistance enhancing agents, particularly in an immunocompromised host resulting from an AIDS-related virus.

U.S. Pat. No. 4,956,355 also dicloses steroids having the same basic steroidal ring structure as the compounds of the present invention, specifically 17-ketosteroids, and their use in treating or arresting the progression of retroviral infections, particularly AIDS and AIDS-related complex.

The compounds employed in the present invention may be synthesized in accordance with procedures generally known and readily understood by those skilled in the art.

The compounds of Formula I are synthesized as shown below by treating the tert-butyldimethylsilyl protected phosphonium salts 1 (Y=polymethylene or related moiety) with n-butyllithium in dimethoxyethane ("DME"), followed by 3-cholestanone (2) or an analogous steroid. The resulting products 3 are then subjected to catalytic hydrogenation over PtO$_2$ catalyst to afford intermediates 4. The tert-butyldimethylsilyl protecting groups of 4 are removed using tetra-n-butylammonium fluoride in THF. The alcohols 5 are converted to the bromides 6 with carbon tetrabromide and triphenylphosphine in methylene chloride. The triphenylphosphinium bromide salts 7 are obtained from intermediates 6 by treatment with triphenylphosphine in chlorobenzene. Deprotonation of phosphonium salts 7 with sodium bis(trimethylsilyl)amide in tetrahydrofuran ("THF") followed by addition of benzophenones 8 yields olefins 9, which either represent compounds of general Formula I or may be converted to compounds of general Formula I.

-continued

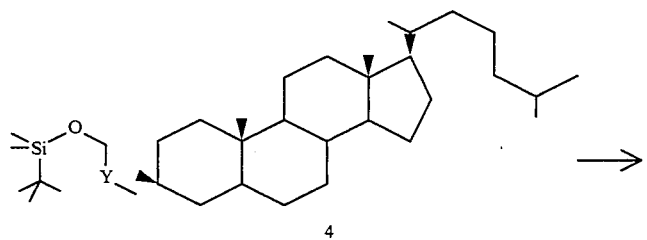
4

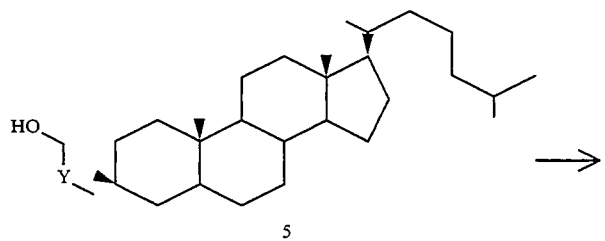
5

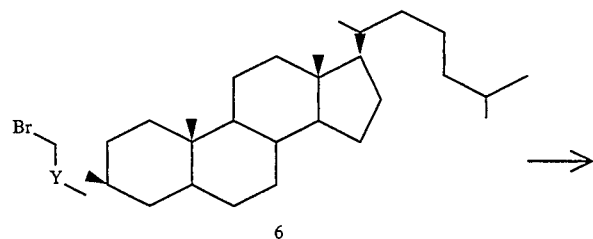
6

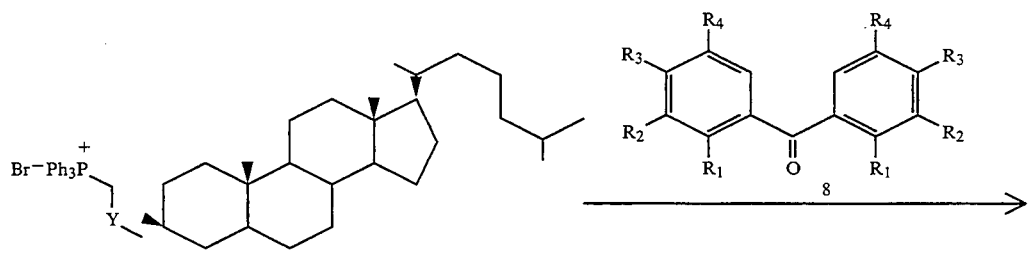
7 8

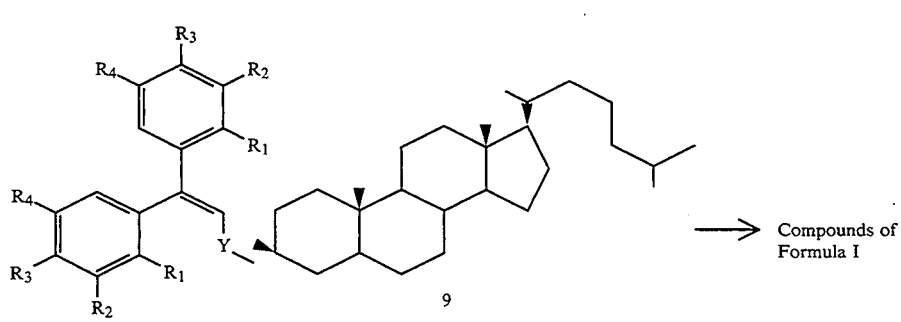
9

⟶ Compounds of Formula I

The compounds of Formula II are synthesized as shown below by reducing the esters 1 (Y=polymethylene or related moiety) with lithium aluminum hydride to afford alcohols 2, which are then converted into the bromides 3 with carbon tetrabromide and triphenyl phosphine. The phosphonium salts 4 are obtained from 3 by treatment with triphenylphosphine in chlorobenzene. Deprotonation of 4 with sodium bis(trimethylsilyl)amide yields the corresponding Wittig ylides, which react with benzophenones 5 to afford intermediates 6. Compounds 6 represent substances of general Formula II or may be converted to compounds of general Formula II.

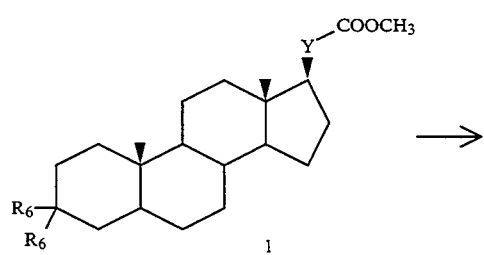
1

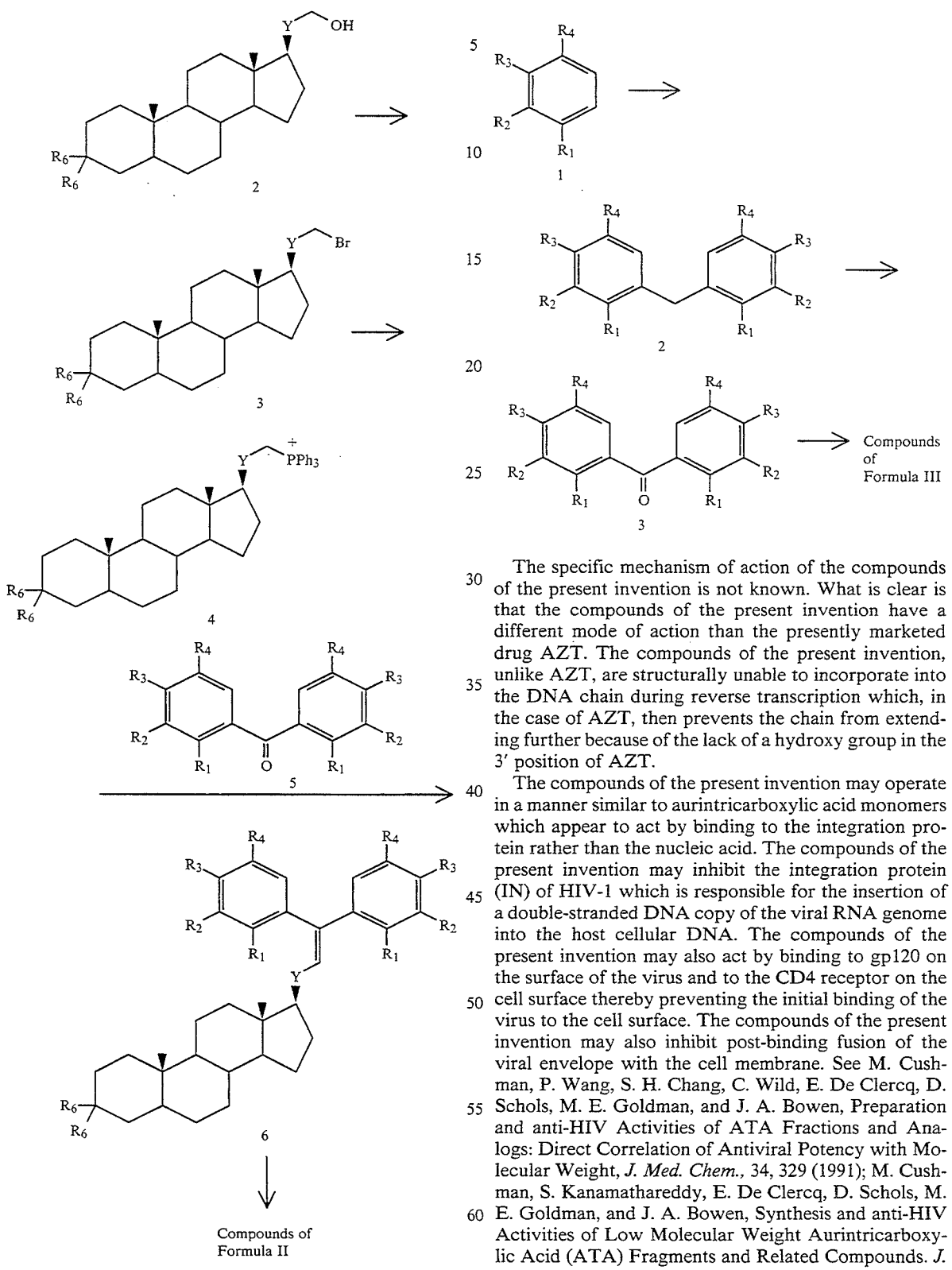

pounds of general Formula III or may be converted to compounds of general Formula III.

The specific mechanism of action of the compounds of the present invention is not known. What is clear is that the compounds of the present invention have a different mode of action than the presently marketed drug AZT. The compounds of the present invention, unlike AZT, are structurally unable to incorporate into the DNA chain during reverse transcription which, in the case of AZT, then prevents the chain from extending further because of the lack of a hydroxy group in the 3' position of AZT.

The compounds of the present invention may operate in a manner similar to aurintricarboxylic acid monomers which appear to act by binding to the integration protein rather than the nucleic acid. The compounds of the present invention may inhibit the integration protein (IN) of HIV-1 which is responsible for the insertion of a double-stranded DNA copy of the viral RNA genome into the host cellular DNA. The compounds of the present invention may also act by binding to gp120 on the surface of the virus and to the CD4 receptor on the cell surface thereby preventing the initial binding of the virus to the cell surface. The compounds of the present invention may also inhibit post-binding fusion of the viral envelope with the cell membrane. See M. Cushman, P. Wang, S. H. Chang, C. Wild, E. De Clercq, D. Schols, M. E. Goldman, and J. A. Bowen, Preparation and anti-HIV Activities of ATA Fractions and Analogs: Direct Correlation of Antiviral Potency with Molecular Weight, *J. Med. Chem.*, 34, 329 (1991); M. Cushman, S. Kanamathareddy, E. De Clercq, D. Schols, M. E. Goldman, and J. A. Bowen, Synthesis and anti-HIV Activities of Low Molecular Weight Aurintricarboxylic Acid (ATA) Fragments and Related Compounds. *J. Med. Chem.*, 34, 337 (1991); M. Cushman and S. Kanamathareddy, Synthesis and Evaluation of a Triphenylcarbinol Related to the Incorrectly Assumed Structure of Aurintricarboxylic Acid, *Ann. N.Y. Acad. Sci.*, 616, 499 (1991); P. Wang, J. Kozlowski, and M. Cushman, Isolation and Structure Elucidation of Low The compounds of Formula III are synthesized as shown below by subjecting the starting materials 1 to formaldehyde and sulfuric acid in methanol to afford intermediates 2, which are then oxidized to the benzophenone derivatives 3. Substances 3 represent com- Molecular Weight Components of Aurintricarboxylic Acid (ATA), *J. Org. Chem.*, 57, 3861 (1992); M. Cushman and P. Sherman, Inhibition of HIV-1 Integration Protein by Aurintricarboxylic Acid (ATA) Monomers, Monomer Analogs, and Polymer Fractions, *Biochem. Biophys. Res. Commun.*, 185, 85 (1992); and M. Cushman, P. Wang, D. Schols, and E. De Clercq, Structural Investigation and Anti-HIV Activities of High Molecular Weight ATA Polymers, *J. Org. Chem.*, 57, 7241 (1992).

One especially important aspect of the present invention is the provision of a method for the treatment of infections by a virus, particularly the human immunodeficiency virus, specifically HIV-1 and HIV-2. The present method includes the administration to an animal, particularly a human, of a therapeutically effective amount of a compound of the present invention.

Another important aspect of the present invention is the provision of a method for preventing infections by a virus, particularly the human immunodeficiency virus, specifically HIV-1 and HIV-2. The present method includes the administration to an animal, particularly a human, of a prophylactically effective amount of a compound of the present invention.

The compounds of the present invention may be administered with or without other anti-viral or anti-retroviral agents to inhibit the growth or replication of a retrovirus, in particular a human immunodeficiency virus, specifically HIV-1 or HIV-2. Such additional anti-retroviral or anti-viral compounds may include AZT, ddi, ddC, gancyclovir, fluorinated dideoxynucleotides, nevirapine, R82913, Ro 31-8959, BI-RJ-70, acyclovir, α-interferon and recombinant CD4.

The compounds of the present invention can be shown to inhibit a retrovirus, such as the human immunodeficiency virus, specifically HIV-1 or HIV-2. As one skilled in the art will appreciate, the compounds of the present invention also may inhibit other retroviruses and may inhibit viruses other than retroviruses. Examples of viruses that may be treated in accordance with the present invention include, but are not limited to, Type C and Type D retroviruses, HTLV-1, HTLV-2, HIV, FLV, SIV, MLV, BLV, BIV, equine infections, anemia virus, avian sarcoma viruses, such as Rous sarcoma virus (RSV), hepatitis type A, B, non-A and non-B viruses, arboviruses, varicella viruses, measles, mumps and rubella viruses as well as CMV and HSV.

The compounds employed in the present invention may be used in the form of their pharmaceutically acceptable salts, may be used alone or in appropriate association, and also may be used in combination with other pharmaceutically active compounds. The active agent may be present in the pharmaceutical composition in any suitable quantity. The pharmaceutically acceptable excipients described herein, for example, vehicles, adjuvants, carriers or diluents, are readily available.

While the method of the present invention can be practiced in vitro, it has particular usefulness in in vivo applications. As regards these applications, the present method includes the administration to an animal, particularly a human, of a therapeutically effective amount of one or more of the aforementioned compounds as an active agent effective against AIDS and AIDS-related infections, particularly an active agent selected from the group consisting of cosalane, and pharmaceutically acceptable derivatives and salts thereof.

One skilled in the art will appreciate that suitable methods of administering a compound of the present invention to an animal are available, and, although more than one route can be used to administer a particular compound, a particular route can provide a more immediate and more effective reaction than another route. Pharmaceutically acceptable excipients are also well-known to those who are skilled in the art, and are readily available. The choice of excipient will be determined in part by the particular compound, as well as by the particular method used to administer the composition. Accordingly, there is a wide variety of suitable formulations of the pharmaceutical compositions of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The dose administered to an animal, particularly a human, in the context of the present invention, should be sufficient to effect a prophylactic or therapeutic response in the animal over a reasonable time frame. One skilled in the art will recognize that dosage will depend upon a variety of factors including the activity of the particular compound employed, the condition of the animal, the body weight of the animal, as well as the severity of the infection and stage of the disease. The size of the dose will also be determined by the existence, nature, and extent of any adverse side-effects that might accompany the administration of a particular compound. The preferred dosage is the amount which results in inhibition of a human immunodeficiency virus, without significant side effects. In proper doses and with suitable administration of certain compounds, the present invention provides for a wide range of the inhibition of the human immunodeficiency virus.

The dose varies, the daily dose being generally 0.1 mg to 500 mg, desirably 1 mg to 30 mg.

The most preferred dosage for extracorporeal administration is in the range from about 0.1 mg/kg to 5 mg/kg of body weight per day. For the oral, rectal, topical (including buccal and sublingual) or transdermal route of administration, the preferred dosage thereof (estimated as the base) is in the range of 0.05 mg/kg to 20 mg/kg of body weight per day. The desired blood serum level is about $1 \times 10^{-6}$ to $1 \times 10^{-4}$ Molar, preferably $1 \times 10^{-6}$ to $1 \times 10_{-5}$ Molar. The dosage sufficient to achieve the desired serum level may be about 250 to 500 mg per day.

All patents or publications cited to or referenced herein are incorporated herein by reference, in their entirety.

The present inventive compounds and methods will be further described in the context of the following examples. These examples serve to illustrate further the present invention and are not intended to limit the scope of the invention.

EXAMPLES in vitro Anti-HIV Testing

The National Cancer Institute's procedure for testing for agents active against Human Immunodeficiency Virus (HIV) (Weislow, O. W. et al, "New soluble-formazan assay for HIV-1 cytopathic effects: application to high-flux screening of synthetic and natural products for AIDS-antiviral activity," *J. Natl. Cancer Inst.*, 81, 577–586, 1989) is designed to detect agents acting at any stage of the virus reproductive cycle. The assay includes the killing of T4 lymphocytes by HIV. Pursuant to the test, small amounts of HIV are added to cells, and a complete cycle of virus reproduction is necessary to obtain the required cell killing. Agents that interact with virions, cells, or virus gene-products to interfere with viral activities will protect cells from cytolysis. The system is thus designed to detect anti-HIV activity. However, compounds that degenerate or are rapidly metabolized in the culture conditions may not show activity in this screen. All tests are compared with at least one positive (e.g., AZT-treated) control done at the same time under identical conditions.

The Procedure

1. The candidate agent is dissolved in dimethyl sulfoxide (unless otherwise instructed), then diluted 1:200 in cell culture medium. Further dilutions (half-log$_{10}$) are prepared before adding to 96-well microtiter plates.

2. T4 lymphocytes (CEM cell line) are exposed to HIV at a virus-to-cell ratio of approximately 0.05 and are plated along with non-infected control cells into drug-containing wells or wells with medium alone.

3. Cultures are incubated at 37° in a 5% carbon dioxide atmosphere for 6 days.

4. The tetrazolium salt, XTT, is added to all wells, and cultures are incubated to allow formazan color development by viable cells.

5. Individual cells are analyzed spectrophotometrically to quantitate formazan production and, in addition, are viewed microscopically for detection of viable cells and confirmation of protective activity.

6. Drug-treated virus-infected cells are compared with drug-treated non-infected cells and with other appropriate controls (untreated infected and untreated non-infected cells, drug-containing wells without cells, etc.) on the same plate.

7. Data are reviewed in comparison with other tests performed at the same time, and a determination about activity is made.

Example 1

This Example illustrates the preparation and anti-HIV activity as indicated by the NCI anti-HIV screen shown above for 1,1-di(3'-ammoniumcarboxy-5'-chloro-4'-hydroxy)phenyl-4-(3β)-cholestanyl-1-butene, Formula IV.

Synthesis of Intermediate Compound A, 1,1-Di(3-carboxy-5-chloro-4-hydroxy)phenylmethane Compound A was prepared by a slight modification of the procedure published by Cushman, M., et al., *Tetrahedron*, 46 1491 (1990). 3-Chlorosalicyclic acid (32.4 g, 0.187 mmol, Aldrich, Note 1) was placed in a 1 L three-necked, round-bottomed flask equipped with a mechanical stirrer, a 500 mL pressure equalizing dropping funnel, and a thermometer. The solid was dissolved in methanol (140 mL), water (25 mL) was added, and the mixture was vigorously stirred at dry ice-acetone bath temperature while concentrated sulfuric acid (325 mL) was added at such a rate to keep temperature below 0° C. The reaction mixture was stirred on an ice bath for 1 hour and then cooled in a dry ice-acetone bath again. An aqueous solution of 37% formaldehyde (75 mL) was added at such a rate to keep the temperature below 0° C. The mixture was stirred at 0° C. for about 4 hours and was left overnight at room temperature. It was poured on crushed ice (1.5 kg) and the precipitate was filtered and dried, first at room temperature overnight and then in a vacuum desiccator, to afford a solid (34.5 g). The product was recrystallized from chloroform-methanol (2:1):mp 296° C.

Synthesis of Intermediate Compound B, 1,1-Di(3-carbomethoxy-5-chloro-4-methoxy)phenylmethane Compound A (1, 8.55 g, 23.95 mmol) was placed in a 500 mL three-necked, round-bottomed flask equipped with a mechanical stirrer, a 50 mL pressure equalizing dropping funnel, and a reflux condenser connected to a drying tube. The acid was dissolved in acetone (240 mL, Mallincrodt, AR), and ground anhydrous potassium carbonate (26.42 g, 191.16 mmol) was added, followed by dimethyl sulfate (16.306 g, 12.23 mL, 129 mmol). The reaction mixture was vigorously stirred under reflux for 2 days. The solvent was removed in vacuo and water (100 mL) was added, followed by methylene chloride (80 mL). The resulting mixture was filtered through a celite pad, the organic phase was separated, the residue on the filtration funnel was washed twice with methylene chloride (2×30 mL), and the second filtrate used for re-extraction of the aqueous phase. The combined organic extracts were washed with water, dried (sodium sulfate) and evaporated in vacuo to yield the product as a colorless solid, 9.24 g. The reaction was scaled up three times without loss of yield. It would be more convenient on scaling up to filter off the inorganic salts from the acetone solution before evaporation of the solvent. The crude product was dissolved in boiling methylene chloride, hexane was added until the solution became turbid, and crystallization came to completion in the refrigerator, yielding pure product (8.2 g, 81%): mp 131°–132° C.; IR (KBr) 2975, 2925, 1730, 1600, 1560, 1480, 1435 1320, 1280, 1250, 1205, 1095, 1000, 925, 835, 790, 725 cm$^{-1}$; $^1$H NMR (500 MHz, CDCl$_3$ δ7.50 (d, J=2.3 Hz, 2H), 7.32 (d, J=2.3, 2H), 3.92 (s, 12H), 3.87 (s, 2H); CIMS m/e (relative intensity) 413 (MH$^+$, 100), 381(71); Anal. Calcd for C$_{19}$H$_{18}$Cl$_2$O$_6$: C, 55.34; H, 4.37. Found C, 55.08; H, 4.45.

Synthesis of Intermediate Compound C, 1,1-Di(3-carbomethoxy-5-chloro-4-methoxy)benzophenone Compound B, (2, 24.99 g, 60.47 mmol) was placed in a 1000 mL one-necked, round-bottomed flask equipped with a Teflon-coated magnetic stirring bar and a reflux condenser connected to a drying tube. Compound B was partially dissolved in acetic anhydride (500 mL, Baker, AR). The mixture was cooled in an ice bath and chromic anhydride (24.26 g, 242.6 mmol) was added in small portions over 0.5 hours. The bath was removed and the mixture was stirred at room temperature for 2 hours and then heated under reflux for 2 hours. After an additional 1 hour, the chromium salts were filtered off and washed with methylene chloride (5×20 mL). The solvent was removed in vacuo and the solidified residue was flash chromatographed on silica gel (300 g). Elution with methylene chloride (2.5L) afforded the benzophenone derivative (18.78 g, 72.8 %): mp 116° C.; IR (KBr) 1744, 1662, 1476, 1269, 988 cm$^{-1}$; $^1$H NMR (500 MHz, CDCl$_3$) δ8.07 (d, J=2.3 Hz, 2H), 7.97 (d, J=2.3 Hz, 2H), 4.03 (s, 6H), 3.94 (s, 6H; CIMS m/e (relative intensity) 427 (M$^+$, 100), 381 (71); Anal Calcd for C$_{19}$H$_{16}$Cl$_2$O$_6$: C, 53.52; H, 3.76. Found: C, 53.28; H, 3.73.

Synthesis of Intermediate Compound D, 3-Bromo-t-butyldimethylsilyl-1-propanol Diisopropylethylamine (25.488 g, 34.35 mL, 0.197 mol) was added dropwise to the solution of 3-bromopropanol (25 g, 0.18 mol), t-butyldimethylsilyl chloride (29.81 g, 0.197 mol), and DMAP (0.880 g, 7.2 mmol) in methylene chloride (250 mL) placed in a dry 500 mL three-necked, round-bottomed flask kept at ice bath and equipped with a Teflon-coated magnetic stirring bar, a 50 mL pressure-equalizing dropping funnel, a stopper, and a reflux condenser connected to an argon flow line. The reaction mixture was stirred at room temperature for 24 hours, washed successively with water (2×150 mL), dilute ammonium chloride solution (1×100 mL), and brine (2×150 mL). The organic solution was dried (sodium sulfate), the solvent was removed in vacuo, and the residual oil was distilled: bp 62°–64° C. (2 mm Hg); ; $^1$H-NMR (CDCl$_3$, 200 MHz) δ3.71 (t, J=6.1 Hz, 2H), 3.46 (t, J=7.0, 2H), 2.00 (m, 2H), 0.87 (s, 9H), 0.06 (s, 6H); CIMS m/e 253.

Synthesis of Intermediate Compound E, 3-t-Butyldimethylsilyloxypropyltriphenylphosphonium Bromide Compound D (2.7 g, 10.75 mmol) and triphenylphosphine (2.83 g, 10.75 mmol) were placed in a 25 mL two-necked, round-bottomed flask equipped with a Teflon-coated magnetic stirring bar, rubber septum, and a reflux condenser connected to an argon flow line. Acetonitrile (3 mL) was added and the solution was heated under reflux for 30 hours. The reaction mixture was cooled to room temperature, the solvent removed in vacuo and oily residue triturated with hexane until crystallization came to completion. The white salt (4.9995 g, 93%) was filtered off on the next day, washed with hexane (3×5 mL), and dried in a vacuum desiccator: mp 137°–139° C.; $^1$H NMR (DMSO-d$_6$, 200 MHz) δ7.9–7.8 (m, 15H), 3.68 (t, J=5.9 Hz, 2H), 3.53 (m, 2H), 1.67 (m, 2H), 0.84 (s, 9H), 0.02 (s, 6H); IR (KBr) 2931, 2858, 1587, 1438, 1254, 1110, 838, 746, 692 cm$^{-1}$; EIMS 435 (M$^+$-Br).

Synthesis of Intermediate Compound F, 3-(3-t-Butyldimethylsilyloxypropenyl-1)-cholestane via Wittig Reaction of Compound E with 3-cholestanone Compound E, (3,896 g, 7.56 mmol) was placed in a dry 250 mL three-necked, round-bottomed flask equipped with a Teflon-coated magnetic stirring bar, 50 mL pressure equalizing dropping funnel capped with a rubber septum, a reflux condenser connected to an argon flow line, and a rubber septum. The apparatus was flushed with argon, and an argon atmosphere was maintained throughout the reaction. Dry DME (40 mL) was added, the suspension was stirred for 5 minutes and n-butyllithium (2.5M, 3.06 mL, Aldrich) was added dropwise with vigorous stirring. The red reaction mixture was stirred for 15 minutes and a solution of 3-cholestanone (2.47 g, 6.3 mmol) in DME (40 mL) was added dropwise. The reaction mixture was heated at 60° C. for 2 days. The reaction mixture was cooled to room temperature and quenched with a solution of ammonium chloride (0.8 g) in water (10 mL). The organic layer was separated and the aqueous extracted once with ether (1×10 mL). 10 mL). The combined organic extracts were washed with brine (2×50 mL) dried (sodium sulfate) and the solvent 5 was removed in vacuo to afford a semisolid (6 g) which was flash-chromatographed on silica gel (300 g). Elution with hexane-acetate ( 6:1 ) yielded the starting ketone (332 mg) and olefin (2.785 g, 80.3 %): mp 58° C. (benzene-ethanol); IR (neat) 2926, 2853, 1668, 1470, 1445, 1383, 1363, 1254, 1100, 835, 775 cm$^{-1}$; $^1$H NMR (CDCl$_3$, 200 MHz) δ4.99 (t, J=7.4 Hz, 1H), 3.57 (t, J=7.4 Hz, 2H), 0.87 (s, 9H), 0.84 (d, J=5.9 Hz, 9H), 0.63 (s, 3H), 0.03 (s, 6H); Anal. Calcd for C$_{36}$H$_{66}$OSi: C, 79.63; H, 12.25. Found: C, 79.67; H, 12.63.

Synthesis of Intermediate Compound G, 3-(3-t-Butyldimethylsilyloxypropyl)-cholestane The Wittig olefin, Compound F, (7, 2.596 g, 4.78 mmol) was dissolved in ethyl acetate (25 mL) and hydrogenated over platinum oxide (Aldrich, 0.486 g) at 50° C., atmospheric pressure for 4 hours The catalyst was filtered off on the Buchner funnel and washed with ethyl acetate (3×3 mL). The solvent removed in vacuo and the colorless product crystallized. The analytical sample was prepared by recrystallization from ethanol-benzene (4:1) mixture: mp 38°–39° C.; IR (neat) 2927, 2854, 1468, 1383, 1254, 1102, 836, 776 cm$^{-1}$; $^1$H NMR (CDCl$_3$, 200 MHz) δ3.56 (t, J=6.3 Hz, 2H), 0.875 (d, J=6.8 Hz, 3H), 0.87 (s, 9H), 0.845 (d, J=6.8 Hz, 3H), 0.72 (s), 0.62 (s, 3H), 0.02 (s, 6H); CIMS m/e (relative intensity) 545 (MH$^+$, 51), 487 (11), 413 (34); Anal. Calcd for C$_{36}$H$_{68}$OSi: C, 79.33; H, 12.57. Found: C, 79.58; H, 12.50.

Synthesis of Intermediate Compound H, 3-(3-Hydroxypropyl)-cholestane

The silyl ether, Compound G, (2.232 g, 4.095 mmol) was dissolved in THF (18 mL) and a 1M solution of tetrabutylammonium fluoride in THF (8.7 mL) was added. The solution was stirred at ambient temperature for 1 hour. THF was removed in vacuo, brine (25 mL) was added and the mixture extracted with benzene (3×15 mL). The combined extracts were washed with brine (2×20 mL), dried (sodium sulfate) and the product obtained after evaporation of the solvent was crystallized from ethanol to afford a solid (1.56 g, 88%): mp 130° C.; IR (KBr) 3302, 2931, 2850, 1466, 1381, 1051 cm$^{-1}$; $^1$H NMR (CDCl$_3$, 200 MHz) $\delta$3.60 (t, J=6.6 Hz, 2H), 1.93 (m, J=12 Hz, 2H), 0.87 (d, J=6.9 Hz, 3H), 0.835 (d, J=6.7 Hz, 6H), 0.715 (s, 3H), 0.616 (s, 3H); EIMS m/e (relative intensity) 430 (M$^+$, 4), 415(6), 272(45), 207(30); Anal. Calcd for C$_{30}$H$_{54}$O: C, 83.65; H, 12.64. Found: C, 84.01; H, 12.54.

Synthesis of Intermediate Compound I, 3-(3-Bromopropyl)-cholestane

Method A. Reaction in acetonitrile: Compound H (1.3 g, 3.018 mmol) and carbon tetrabromide (2.007 g) were placed in a dry 250 mL three-necked, round-bottomed flask equipped with a Teflon-coated magnetic stirring bar, 50 mL pressure-equalizing dropping funnel capped with a rubber septum, a reflux condenser connected to an argon flow line, and a rubber septum. Acetonitrile (70 mL, dried over molecular sieves) was added, the mixture was heated under reflux, and a solution of triphenylphosphine (2.38 g) in acetonitrile (50 mL) was added dropwise with stirring over 10 minutes. The yellow solution was heated under reflux for 1.5 hours and cooled to room temperature. The solvent was removed in vacuo and the reaction mixture was extracted with benzene (4×20 mL). The extracts were filtered and evaporated in vacuo. The solid residue was flash-chromatographed on silica gel (90 g). Elution with hexane-ethyl acetate (4:1) afforded the light sensitive product as a crystallizing oil (1.47 g). Crystallization from acetone afforded the pure bromide (1.17 g, 79%): mp 45° C.; IR (KBr) 2931, 2850, 1464, 1381, 1237 cm$^{-1}$; $^1$H NMR (CDCl$_3$, 200 MHz) $\delta$3.39 (t, J=6.9 Hz, 2H), 0.895 (d, J=6.8, 3H), 0.86 (d, J=6.8, 6H), 0.74 (s, 3H), 0.64 (s, 3H); CIMS m/e (relative intensity) 493 (MH$^+$, 100), 413 (91); Anal. Calcd for C$_{30}$H$_{53}$Br: C, 72.99; H, 10.82. Found: C, 73.13; H, 10.79.

Method B. Reaction in methylene chloride: Compound H (1.402 g, 3.255 mmol) and carbon tetrabromide (1.471 g, 4.435 mmol) were placed in a dry 50 mL two-necked, round-bottomed flask equipped with a Teflon-coated magnetic stirring bar, a reflux condenser connected to an argon flow line, and a rubber septum. Methylene chloride (20 mL, dried over phosphorous pentoxide) was added, the solution was cooled in an ice-bath, and a solution of triphenylphosphine (1.279 g, 4.876 mmol) in methylene chloride (8 mL) was added dropwise over one minute. The yellow solution was stirred at 0° C. for 10 minutes and the solvent was removed in vacuo. The residue worked up as above to yield the product (1.571 g, 98%). The product is light sensitive.

Synthesis of Intermediate Compound J, 3-(3-propyl)cholestanyltriphenylphosphonium bromide Compound I (291.5 mg, 0.591 mmol) and triphenylphosphine (155 mg, 0.591 mmol) were dissolved in chlorobenzene (1 mL) and the solution was heated at reflux for 3 days under argon with stirring. The solvent was removed in vacuo. The residue was triturated with hexane, filtered, and washed with hexane to afford a solid (416 mg, 93%). The analytical sample was prepared by crystallization from acetone: mp 274° C.; IR (KBr) 3055, 2927, 2865, 1438, 1190, 1118, 751, 722, 696 cm$^{-1}$; $^1$H NMR (CD$_3$OD, 200 MHz) $\delta$7.9–7.7 (m, 15H), 3.35 (m, 2H), 0.90 (d, J=8.5 Hz, 3H), 0.886 (d, J=6.3 Hz, 6H), 0.74 (s, 3H), 0.66 (s, 3H); PDMS m/e (relative intensity) 676 (MH$^+$, 100); Anal. Calcd for C$_{48}$H$_{68}$BrP: C, 76.26; H, 9.07. Found: C, 76.28; H, 9.42.

Synthesis of Intermediate Compound K, 1,1-Di(3'-carbomethoxy-5'-chloro-4'-methoxy)phenyl-4-(3$\beta$)-cholestanyl-1-butene The phosphonium salt, Compound J, (343 mg, 0.454 mmol) was placed in a dry 25 mL two-necked, round-bottomed flask equipped with a Teflon-coated magnetic stirring bar, a reflux condenser connected to an argon flow line, and a rubber septum. The apparatus was flushed with argon, and the argon atmosphere was maintained throughout the reaction. THF (9 mL, freshly distilled from sodium-benzophenone) was added via the septum, the suspension of the phosphonium salt was cooled in an ice bath and a 1M solution of sodium bis(trimethylsilyl)amide in THF (0.454 mL) was added dropwise. The orange solution was stirred for 15 minutes and a solution of the ketone, Compound C, (194 mg, 0.454 mmol) in THF (5 mL) was added dropwise via the septum/syringe. The bath was removed and the reaction mixture was stirred at room temperature overnight. It was quenched with a solution of ammonium chloride (0.5 g) in water (5 mL). The organic layer was separated and the aqueous one extracted with ether (1×5 mL). The combined organic extracts were washed with brine (2×15 mL), dried (sodium sulfate) and the solvent was removed in vacuo to yield a yellowish solid (0.45 g) which was flash chromatographed on silica gel. Elution with hexane-ethyl acetate mixture (6:1) afforded an alkene dimer (7 mg), 1,1-di(3$\beta$-cholestanyl)-3-hexene, Wittig product, Compound K, (0.254 g, 68%), and the starting ketone (40 mg). The olefin, Compound K, was crystallized from hexane-ethyl acetate: mp 152°–153° C.; IR (KBr) 2930, 2852, 1735, 1656, 1474, 1438, 1254, 1210, 1092, 1001, 745 cm$^{-1}$; $^1$H NMR (CDCl$_3$, 500 MHz) $\delta$7.49 (d, J=2.3 Hz, 1H), 7.475 (d, J=2.1 Hz, 1H), 7.32 (d, J=2.1 Hz, 1H), 7.295 (d, J=2.3 Hz, 1H), 6.06 (t, J=7.6 Hz, 1H), 4.00 (s, 3H), 3.93 (s, 3H), 3.92 (s, 3H), 3.915 (s, 3H), 2.045 (m, 2H), 1.95 (m, 1H), 0.89 (d, J=7.0, 3H), 0.86 (dd, J=7.0; 2.2 Hz, 6H), 0.72 (s, 3H), 0.64 (s, 3H); FABMS m/e (relative intensity) 823 (MH$^+$, 5); Anal. Calcd for C$_{49}$H$_{68}$Cl$_2$O$_6$: C, 71.42; H, 8.32. Found: C, 71.46; H, 8.60. When the reaction was repeated on a 3 mmol scale, a yield of 70% was obtained.

Synthesis of 1,1-Di(3'-carboxy-5'-chloro-4'-hydroxy) phenyl-4 (3$\beta$) -cholestanyl-1-butene and the Ammonium Salt, Structure IV Cosalane)

A solution of boron tribromide-dimethyl sulfide complex (1M, 3.2 mL) was placed in a dry 25 mL two-necked, round-bottomed flask equipped with a Teflon-coated magnetic stirring bar, a reflux condenser connected to an argon flow line, and a rubber septum. Dry, 1,2-dichloroethane (12 mL) was added, followed by a solution of ester K (311 mg, 0.377 mmol) in 1,2-dichloroethane (4 mL). The mixture was stirred at 90° C. (oil bath) for 8 hours, and at room temperature overnight. Water (10 mL) was added with ice bath cooling and the mixture was stirred at room temperature for 1 hour. The product was extracted with ethyl acetate (4×10 mL) and the combined extracts were dried (sodium sulfate). The crude product obtained after evaporation of the solvent in vacuo (290 mg) was crystallized from acetone-chloroform mixture to afford the first crop (135 mg), mp 265°–267° C.; IR (KBr) 3500–2500, 2925, 1664, 1606, 1444, 1378, 1231, 1179, 899, 798 cm$^{-1}$, $^1$H NMR (CDCl$_3$, 200 MHz) $\delta$7.71 (d, J=2 Hz, 1H), 7.69 (d, J=2.2 Hz, 1H), 7.59 (d, J=2.2 Hz, 1H), 7.59 (d, J=2.2 Hz, 1H), 7.51 (d, J=2 Hz, 1H), 6.19 (t, J=7.6 Hz, 1H), 2.17 (m, 2H), 0.93 (d, J=6.5 Hz, 3H), 0.87 (d, J=6.6 Hz, 6H), 0.76 (s, 3H), 0.68 (s, 3H); FABMS m/e (relative intensity) 767 (MH$^+$, 10), 749 (13); Anal. Calcd for C$_{45}$H$_{60}$Cl$_2$O$_6$: C, 70.39; H, 7.88. Found: C, 70.20; H, 8:19. The mother liquors were concentrated and the residue (150 mg) was flash-chromatographed on silica gel (15 g). Elution with chloroform-THF-97% formic acid (300:15:1) afforded another 126 mg of pure diacid (overall yield 90%). The ammonium salt was prepared by dissolving the diacid in ammonia (1 mL) and evaporation of the solution in vacuo, mp 200° C.

The title compound Cosalane was subjected to anti-HIV testing as defined above. The following results were obtained.

| Run | IC$_{50}$ (Molar) | EC$_{50}$ (Molar) | TI$_{50}$ (IC/EC) |
|---|---|---|---|
| 1 | >3.10 × 10$^{-4}$ | 3.10 × 10$^{-6}$ | >1.00 × 10$^2$ |
| 2 | >3.10 × 10$^{-4}$ | 6.70 × 10$^{-6}$ | >4.70 × 10$^{+1}$ |
| 3 | >3.10 × 10$^{-4}$ | 6.20 × 10$^{-6}$ | >5.00 × 10$^{+1}$ |
| 4 | >3.10 × 10$^{-4}$ | 6.70 × 10$^{-6}$ | >4.70 × 10$^{+1}$ |

Activity was also examined by determination of p24 and reverse transcriptase concentrations.

To determine p24, a p24 antigen-capture assay was used. Culture fluids harvested from drug test plates or other sources were diluted 1:100 in 10% triton X-100 and stored frozen at −70° C. 200 μL aliquots of the triton treated samples were added in duplicate to microtiter wells previously coated with rabbit polyclonal anti-HIV-1 p24 serum and incubated at room temperature overnight. After washing and blotting, 100 μL of biotinylated polyclonal anti-HIV p-24 was added to each of the appropriate wells, and the plates were re-incubated at 37° C. for 60 minutes. A solution of streptavidin-horseradish peroxidase was added after additional washing and blotting. The contents of each plate were mixed and reincubated for 15 minutes at room temperature and, after washing and blotting, the o-phenylenediamine dihydrochloride substrate was added in 100 μL aliquots. Color was allowed to develop in the dark room at room temperature for 30 minutes, and the reaction was halted by the addition of 4 N H$_2$SO$_4$. Optical density was measured at 490 nm, and the concentration of p24 was determined by comparison with a standard curve of known concentrations of p24. Eislow, O., et al., *J. Nat'l Cancer Inst.*, 81 (8):577–86 (1989).

Reverse transcriptase assays were performed according to the method of Hoffman et al, *Virology*, 147, 326–335 (1985), with minor modifications. Briefly, 15 μl of cell-free supernatant was mixed with 10 μl of RT reaction buffer. The total 25 μl reaction mixture consisted of 2.5 μCi of tritated thymidine triphosphate (TTP) (ICN, 80 Ci/mmol), poly rA (50 ng/ml):oligo dT (10 ng/ml) template:primer (Pharmacia), 10 mM Tris, pH 7.6, 8 mM magnesium chloride, 10 mM dithiothreitol (DTT), and, in the standard reaction, 0.5% Triton X-100. Assays were performed in the absence of added EGTA unless indicated. When EGTA (Sigma) was added it was at a concentration of 1 mM. The reactions were incubated for 60 minutes at 37° C. The reaction volume was then spotted onto DE81 chromatography paper (Whatman), washed extensively in 5% dibasic sodium phosphate, and counted for incorporated radioactivity in a toluene-based scintillation cocktail. Assays were also performed to measure the presence of a nuclease activity associated with HIV virions. These assays included the preincubation of the individual RT reaction components (tritiated TTP, poly rA, oligo dT, poly rA:oligo dT, reaction buffer) with virions, and also the mixing of virions with the reaction product generated by purified RT from avian myeloblastosis virus (AMV). The AMV RT product was made by allowing AMV RT to polymerize using poly rA:oligo dT as template:primer and [$^3$H]TTP as substrate for 60 minutes at 37° C. AMV RT was then inactivated by heating to 60° C. for 5 minutes. The HIV virion sample was added to the AMV RT reaction product and the amount of radioactivity able to bind to DE81 paper was monitored after varying times of incubation at 37° C. Prior heating to 60° C. had no effect on the product. R. W. Buckheit, Jr. and R. Swanstrom, *AIDS Research and Human Retrovirus*, 295–302 (1991).

Example 2

This Example illustrates the preparation and anti-HIV activity as indicated by the NCI anti-HIV screen shown above for (5α-3β-[4,4-Di(3'-ammoniumcarboxy-5'-chloro-4'-methoxy)phenyl-1-buten-3-yl]cholestane, Formula V.

Synthesis of the Compound of Formula V

The diacid precursor of the salt represented by Formula V was obtained by hydrolysis of the corresponding dimethyl ester: mp 113°–114° C. (methanol-methylene chloride): IR (KBr) 3500–2600, 2929, 2858, 1702, 1475, 1377, 1256, 1001 cm$^{-1}$; $^1$H NMR (acetone-d$_6$, 500 MHz) $\delta$7.61 (d, J=2.0 Hz, 1H), 7.60 (d, J=2.5 Hz, 1H), 7.52 (d, J=2.5 Hz, 1H), 7.515 (d, J=2Hz, 1H), 6.30 (t, J=8 Hz, 1H), 3.98 (s, 3H), 3.92 (s, 3H), 0.82 (d, J=6.5 Hz, 3H), 0.93 (d, J=6.5 Hz, 3H), 0.87 (dd, J=7.0; 2.0 Hz, 6H), 0.76 (s, 3H), 0.68 (s, 3H), FABMS m/e (relative intensity) 794 (M$^+$, 5), 777 (MH$^+$-H$_2$O); Anal. Calcd for C$_{47}$H$_{64}$O$_6$Cl$_2$×½ H$_2$O: C, 70.13; H, 8.14. Found: C, 70.27; H, 8.25.

The ammonium salt represented by formula V was prepared by dissolving the diacid in ammonia and evaporation of the solution in vacuo. The compound of Formula V was subjected to anti-HIV testing as defined above. The following results were obtained.

| Run | IC$_{50}$ (Molar) | EC$_{50}$ (Molar) | TI$_{50}$ (IC/EC) |
|---|---|---|---|
| 1 | >3.00 × 10$^{-4}$ | 1.30 × 10$^{-5}$ | >2.40 × 10$^{+1}$ |
| 2 | >3.00 × 10$^{-4}$ | 1.80 × 10$^{-5}$ | >1.70 × 10$^{+1}$ |
| 3 | >3.00 × 10$^{-4}$ | 2.20 × 10$^{-5}$ | >1.40 × 10$^{+1}$ |
| 4 | >3.00 × 10$^{-4}$ | 1.90 × 10$^{-5}$ | >1.60 × 10$^{+1}$ |
| 5 | >3.00 × 10$^{-4}$ | 6.10 × 10$^{-6}$ | >5.00 × 10$^{+1}$ |

| Run | IC$_{50}$ (Molar) | EC$_{50}$ (Molar) | TI$_{50}$ (IC/EC) |
| --- | --- | --- | --- |
| 6 | >3.00 × 10$^{-4}$ | 5.50 × 10$^{-6}$ | >5.50 × 10$^{+1}$ |

Example 3

This Example illustrates the preparation and anti-HIV activity as indicated by the NCI anti-HIV screen shown above for (5α)-3β-[4,4-Di(3'-ammoniumcarboxy-5'-chloro-4'-hydroxy)phenyl-1-butyl]cholestane, Formula VI.

Synthesis of Intermediate Compound A, (5α)-3β-[4,4-di(5-chloro-4-methoxy-3-methoxycarbonyl)phenyl]-1-butyl]cholestane The Wittig olefin, (5α)-3β-[4,4-di(5-chloro-4-methoxy-3 -methoxycarbonylphenyl-1-buten-3-yl]cholestane (68 mg) was hydrogenated with Adams catalyst (18 mg) in ethyl acetate (8 mL) at room temperature. The catalyst was filtered off, washed with ethyl acetate and the filtrate was evaporated in vacuo to yield solid (67 mg). An analytical sample was prepared by crystallization from hexane-ethyl acetate mixture: mp 113°-114° C.; IR (KBr) 2931, 2858, 1733, 1473, 1259, 1198, 1001 cm$^{-1}$; $^1$H NMR (CDCl$_3$, 200 MHz) δ7.45 (d, J=2.0 Hz, 2H), 7.275 (d, J=2Hz, 2H), 3.86 (s, 6H), 3.84 (s, 6H), 3.75 (t, J=7.6 Hz, 1H), 0.82 (d, J=6.5 Hz, 3H), 079 (d, J=6.5 Hz, 6H); 0.65 (s, 3H), 0.56 (s, 3H); FABMS m/e (relative intensity) 824 (M$^+$,9); Anal Calcd for C$_{49}$H$_{70}$O$_6$Cl$_2$: C, 71.25; H, 9.54. Found: C, 71.48; H, 8.87.

Synthesis of Intermediate Compound B, (5α)-3β-[4,4-di(3-carboxy-5-chloro-4-hydroxy)phenyl-1-butyl]cholestane Boron tribromide-dimethyl sulfide complex (1M solution in methylene chloride, 1.54 mL) was added dropwise to a stirred solution of diester, Compound A above, (0,108 g, 0,131 mmol) in dichloroethane (9 mL) and the mixture was stirred at 70° C. for 8 hours and at room temperature overnight. It was cooled in ice, quenched with water (5 mL), and stirred for 1 hour. Ethyl acetate was added to dissolve the precipitation and the organic layer was separated. The aqueous layer was extracted with chloroform (1×5 mL). The combined organic extracts were washed with water, dried (sodium sulfate) and evaporated to dryness. The solid residue (0.11 g) was flash chromatographed on silica gel (10 g). Elution with chloroform-THG-97 % formic acid (150:30:0.5) yielded the pure diacid, Compound B above, 77 mg (76.5%). An analytical sample was prepared by crystallization from methylene chloride: mp 252° C.; IR (KBr) 3500–2600, 2928, 2852, 1667, 1609, 1443, 1236, 1182, 712 cm$^{-1}$; $^1$H NMR (acetone-d$_6$, 200 MHz) δ7.84 (broad s, 2H) , 7.67 (broad s, 2H), 4.05 (t, J=8.0 Hz, 1H), 0.915 (d, J=6.5 Hz, 3H), 0.85 (d, J=6.5 Hz, 6H), 0.74 (s, 3H), 0.66 (s, 3H; FABMS m/e (relative intensity) 791 (MH$^+$+Na, 5), 768 (MH$^+$, 1.5), 752 (MH$^+$-H$_2$O, 1.5); Anal. Calcd for C$_{45}$H$_{62}$Cl$_2$O$_6$: C, 70.20; H, 812. Found: C, 70.49; H, 8.28. The ammonium salt showed mp 242° C.

The ammonium salt represented by formula VI was prepared by dissolving the diacid in ammonia and evaporation of the solution in vacuo. The compound of Formula VI was subjected to anti-HIV testing as defined above. The following results were obtained.

| Run | IC$_{50}$ (Molar) | EC$_{50}$ (Molar) | TI$_{50}$ (IC/EC) |
| --- | --- | --- | --- |
| 1 | >3.10 × 10$^{-4}$ | 1.70 × 10$^{-5}$ | >1.80 × 10$^{+1}$ |
| 2 | >3.10 × 10$^{-4}$ | 1.50 × 10$^{-5}$ | >2.10 × 10$^{+1}$ |
| 3 | >3.10 × 10$^{-4}$ | 2.30 × 10$^{-5}$ | >1.30 × 10$^{+1}$ |
| 4 | >3.10 × 10$^{-4}$ | 2.50 × 10$^{-5}$ | >1.20 × 10$^{+1}$ |

Example 4

This Example illustrates the preparation and anti-HIV activity as indicated by the NCI anti-HIV screen shown above for (5α)-3β-[4,4-di(5'-bromo-4'-methoxy-3'-methoxycarbonyl)phenyl-1-buten-3-yl]cholestane, Formula VII.

Synthesis of Intermediate Compound A, (5α)-3β-[4,4-di(5'-bromo-4 '-methoxy-3 '-methoxycarbonyl)phenyl-1-buten-3yl]cholestane A solution of the phosphonium salt, 3-(-propyl) cholestanyltriphenylphosphonium bromide, (0,485 g, 0.64 mmol) in dry THF (13 mL) was treated with sodium bis(trimethylsilyl)amide (1M solution, 0.64 mL) for 30 min at 0° C. A solution of the di(5'-bromo-4'-methoxy-3'methoxycarbonyl)phenyl ketone (0.330 g, 0.64 mmol) in dry THF (5 mL) was added dropwise and the mixture was stirred at room temperature for 2 days. It was quenched with a solution of ammonium chloride (60 mg) in water (3 mL). The organic layer was separated and the aqueous one extracted with ether (1×5 mL). The combined organic extracts were washed with brine (2×5 mL), dried (sodium sulfate) and the solvent was evaporated in vacuo to afford 0.72 g of an oil which was flash chromatographed on silica gel (45 g). Elution with hexane-ethyl acetate (6:1) yielded intermediate A, (323 mg, 55%) as a glass: IR (KBr) 2928, 2854, 1735, 1462, 1285, 1251, 1006 cm$^{-1}$; $^1$H NMR (CDCl$_3$, 200 MHz) δ7.86 (d, J=2.5 Hz, 1H) , 7.77 (d, J=2.3 Hz, 1H), 7.53 (d, J=2.5 Hz, 1H), 7.47 (d, J=2.3 Hz, 1H), 6.02 (t, J=7.6 Hz, 1H), 3.85 (s, 6H), 3.48 (s, 3H), 3.46 (s 3H), 0.87 (d, J=6.7 Hz, 3 H), 0.83 (d, J=6.6 Hz, 6H), 0.705 (s, 3H), 0.61 (s, 3H); FABMS m/e (relative intensity) 913 (MH$^+$, 6), 881 (MH$^+$-CH$_3$OH, 55); Anal. Calcd for C$_{49}$H$_{68}$Br$_2$O$_6$: C, 64.47; H, 7.51. Found: C, 64.26; H, 7.71.

Synthesis of Compound B, (5α)-3β-[4,4-di(5'-bromo-3'-carboxy-4 '-hydroxy)phenyl-1-buten-3-yl]cholestane and its Ammonium Salt.

Boron tribromide-dimethyl sulfide complex (1M solution in methylene chloride, 3.5 mL) was added dropwise to a stirred solution of intermediate A, (0.214 g, 0.234 mmol) in dichloroethane (9 mL) and the mixture was stirred at 65° C. for 21 hours. The reaction mixture was cooled in ice, quenched with water (5 mL), and stirred for 1 hour. Ethyl acetate was added to dissolve a precipitation and the organic layer was separated. The aqueous layer was extracted with chloroform (1×5 mL). The combined organic extracts were washed with water, dried (sodium sulfate) and evaporated to dryness. The solid residue (0.21 g) was flash chromatographed on silica gel (7 g). Elution with chloroform-THF-97% formic acid (150:30:0.5) yielded pure diacid, 106 mg (76.5%). An analytical sample was prepared by crystallization from methylene chloride: mp 195° C.; IR (KBr) 3500–2600, 2926, 2852, 1660, 1608, 1429, 1221, 1177, 686 cm$^{-1}$; $^1$H NMR (acetone-d$_6$, 200 MHz) δ7.95 (broad s, 1H), 7.89 (broad s, 1H), 7.59 (m, 2H), 6.10 (t, J=7.8 Hz, 1H), 0.92 (d, J=6 Hz, 3H), 0.855 (d, J=6.5 Hz, 6H), 0.736 (s, 3H), 0.665 (s, 3H); FABMS m/e (relative intensity) 857 (MH+, 15), 839 (MH+-H$_2$O, 35); Anal. Calcd for C$_{45}$H$_{60}$Br$_2$O$_6$ ×H$_2$O: C, 61.79; H, 7,14. Found: C, 61.81; H, 7.38. The ammonium salt showed mp 191°–193° C.

The ammonium salt represented by Formula VII was prepared by dissolving the diacid in ammonia and evaporation of the solution in vacuo. The compound of Formula VII was subjected to anti-HIV testing as defined above. The following results were obtained.

| Run | IC$_{50}$ (Molar) | EC$_{50}$ (Molar) | TI$_{50}$ (IC/EC) |
| --- | --- | --- | --- |
| 1 | >2.80 × 10$^{-4}$ | 4.20 × 10$^{-5}$ | >6.70 × 10$^0$ |
| 2 | >2.80 × 10$^{-4}$ | 1.70 × 10$^{-5}$ | >1.70 × 10$^{+1}$ |
| 3 | >2.80 × 10$^{-4}$ | 3.10 × 10$^{-5}$ | >9.20 × 10$^0$ |
| 4 | >2.80 × 10$^{-4}$ | 3.80 × 10$^{-5}$ | >7.30 × 10$^0$ |
| 5 | >2.80 × 10$^{-4}$ | 6.40 × 10$^{-6}$ | >4.40 × 10$^{+1}$ |
| 6 | >2.80 × 10$^{-4}$ | 1.50 × 10$^{-5}$ | >1.80 × 10$^{+1}$ |

Example 5

This Example illustrates the preparation and anti-HIV activity as indicated by the NCI anti-HIV screen shown above for (5α)-3β-[4,4-di(3'-ammoniumcarboxy-5'-chloro-4'-hydroxy)phenyl-1-butene-3-yl]cholestane, Formula VIII.

Synthesis of Intermediate Compound A, (5α)-3-Ethoxycarbonylmethylenecholestane

Method A. Acid catalyzed reaction

This compound was prepared by modification of the published procedure (Bose, A. K., Dahill, R. T. J. *J. Org. Chem.*, 30, 505 (1965). DME was used as a solvent in place of benzene and reaction time was extended to three days; yield 67%: mp 73°–74° C.; lit. mp 83°–85° C.; IR (KBr) 2929, 2858, 1649, 1462, 1382, 1219, 1147, 1038 cm$^{-1}$; $^1$H NMR (CDCl$_3$, 500 MHz) δ5.58 (m, 1H), 4.13 (q, J=7 Hz, 2H), 1.27 (t, J=7.0 Hz, 3H), 0.904 (s, 3H), 0.895 (d, J=6.5 Hz, 3H); 0.86 (dd, J=6.5; 2.0 Hz, 6 h), 0.0654 (s, 3H), 0.56 (s, 3H); CIMS m/e (relative intensity) 456 (MH+, 88 ).

Method B. Base catalyzed reaction The reaction followed the published procedure, THF was used as a solvent for cholestan-3-one. The identical product as above was obtained in 93.6% yield.

Synthesis of Intermediate Compound B, (5α)-3-Ethoxycarbonylmethylcholestane

The olefin, Compound A above, (4.22 g) was hydrogenated with Adams catalyst (0.8 g) in ethyl acetate (30 mL) at room temperature. The catalyst was filtered off, washed with ethyl acetate, and the filtrate was evaporated in vacuo to yield an oil (4.109 g). An analytical sample was prepared by crystallization from methanol-ethyl acetate mixture, mp 81°–83° C.; IR (KBr) 2930, 2853, 1731, 1465, 1379, 1299, 1175, 1031 cm$^{-1}$; $^1$H NMR of the major isomer (CDCl$_3$, 500 MHz) δ4.10 (q, J=7.0; 2 Hz, 2H), 1.23 (t, J=7.0 Hz, 3H), 0.87 (d, J=6.5 Hz, 3H), 0.84 (dd, J=6.5; 2.0 Hz, 6H); 0.76 (s, 3H), 0.62 (s, 3H); CIMS m/e (relative intensity) 459 (MH+, 100); Anal Calcd for C$_{31}$H$_{54}$O$_2$: C, 81.16; H, 11.86. Found: C,81.10; H, 12.05.

Synthesis of Intermediate Compound C, (5α)-3-(2-hydroxyethyl)cholestane

A solution of the ester, Compound B above, (4.324 g, 9.422 mmol) in dry THF (30 mL) was added dropwise to 1M solution of LAH in ether (12.4 mL) and the mixture was stirred at 0° C. for 1 hour. The reaction mixture was quenched with water (0.48 mL), 15% sodium hydroxide (0.48 mL), and water (1.43 mL), diluted with methylene chloride (10 mL), filtered, and a precipitate on the filter was washed with methylene chloride (3×5 mL). The filtrate was evaporated to dryness to afford the alcohol, Compound C, as a white solid (3.594 g, 91.3%): mp 94° C. (abs. ethanol); IR (KBr) 3332, 2926, 2853, 1462, 1378, 1299, 1062 cm$^{-1}$; $^1$H NMR of the major isomer (CDCl$_3$, 200 MHz) δ3.66 (t, J=6.7 Hz, 2H), 0.86 (d, J=6.7 Hz, 3H), 0.89 (d, J=6.7 Hz, 6H); 0.78 (s, 3H), 0.637 (s, 3H); CIMS m/e (relative intensity) 459 (MH+-EtOH, 7.9); Anal. Calcd for C$_{29}$H$_{52}$O:C, 83.58; H, 12.58. Found: C, 83.26; H, 12.72.

Synthesis of Intermediate Compound D, (5α)-3-(2-bromoethyl)cholestane

A solution of triphenylphosphine (3,370 g, 12.85 mmol) in dry methylene chloride (16 mL) was added dropwise with stirring to the solution of alcohol (3,594 g, 8,624 mmol) and carbon tetrabromide (3,575 g, 10.78 mmol) in dry methylene chloride (12 mL) at 0° C. The mixture was stirred in an ice bath for 10 minutes, solvent was removed in vacuo and the residue was stirred with ether (5×6 mL). The combined organic extracts were filtered, evaporated in vacuo and flash chromatographed on silica gel (250 g) to afford the product (3.85 g, 93%). An analytical sample was obtained by crystallization from acetone: mp 75°–76° C.; IR (KBr) 2930, 2856, 1461, 1377, 1260 cm$^{-1}$; $^1$H NMR of the major isomer (CDCl$_3$, 500 MHz) δ3.39 (t, J=6.7 Hz, 2H), 0.88 (d, J=7 Hz, 3H), 0.89 (dd, J=7; 2.5 Hz, 6H); 0.76 (s, 3H), 0,616 (s, 3H); CIMS m/e (relative intensity) 479 (MH+, 81) 399 (MH+-Br); Anal Calcd for C$_{29}$H$_{51}$Br: C, 72,62; H, 10.72. Found: C, 72.81; H, 11.10.

Synthesis of Intermediate Compound E, (5α)-3-(2-triphenylphosphoniumethyl)cholestane bromide A solution of triphenylphosphine (1,908 g, 7,276 mmol) and bromide, Compound D above, (3.490 g, 7.276 mmol) in chlorobenzene (7 mL) was heated at 140° C. for 24 hours. The solvent was removed in vacuo and the residue was triturated with hexane. The phosphonium salt was filtered, washed with hexane, and dried in vacuum desiccator, 4.249 g (78.7%), mp 150° C.; IR (KBr) 2928, 2861, 1626, 1439, 1378, 1190, 744, 692 cm$^{-1}$; $^1$H NMR of the major isomer (CDCl$_3$, 200 MHz) δ7.9–7.8 (m, 15H), 3.75 (m, 2H), 0.86 (d, J=5.3 Hz, 3H), 0.83 (d, J=6.3 Hz, 6H); 0.69 (s, 3H), 0,585 (s, 3H); FABMS m/e (relative intensity) 661 (M+, 100).

Synthesis of Intermediate Compound F, (5α)-3β-[3,3-di (5'-chloro-4'-methoxy-3'-methoxycarbonyl)phenyl-1-propen-2-yl]cholestane A solution of the phosphonium salt, Compound E, (0,378 g, 0.51 mmol) in dry THF (9 mL) was treated with sodium bis(trimethylsilyl)amide (1M solution, 0.51 mL) for 30 minutes at 0° C. A solution of the ketone, 1,1-di(5-chloro-4-methoxy-3-methoxycarbonyl) benzophenone, (0,218 g, 0.51 mmol) in dry THF (5 mL) was added dropwise and the mixture was stirred at room temperature for 2 days. It was quenched with a solution of ammonium chloride (60 mg) in water (3 mL). The organic layer was separated and the aqueous one extracted with ether (1×5 mL). The combined organic extracts were washed with brine (2×5 mL), dried (sodium sulfate) and the solvent was evaporated in vacuo to afford 0.58 g of a semisolid which was flash chromatographed on silica gel (28 g). Elution with hexane-ethyl acetate (6:1) yielded an alkene, Compound F, as a glass, 0.24 g (63.4%), which was crystallized twice from hexane-ethyl acetate-ethanol: mp 96°–98° C.; IR (KBr) 2932, 2862, 1735, 1475, 1438, 1261, 1206, 1001 cm$^{-1}$; $^1$H NMR of the major isomer (CDCl$_3$, 500 MHz) $\delta$7.47 (m, 1H), 7.45 (m, 1H), 7.30 (m, 1H), 7.27 (m, 1H), 6.07 (t, J=7.6 Hz, 1H), 3.986 (s, 3H), 3.913 (s, 6H), 3.906 (s, 3H), 0.91 (s, 3H), 0.86 (d, J =6.5 Hz, 3H), 0.84 (dd, J=6.5; 2.0 Hz, 6H), 0.72 (s, 3H), 0.59 (s, 3H); FABMS m/e (relative intensity) 809 (MH$^+$, 19), 777 (MH$^+$-CH$_3$OH, 100); Anal Calcd for C$_{48}$H$_{66}$Cl$_2$O$_6$: C, 71.18; H, 8.21. Found C, 71.19; H, 8.25.

Synthesis of Intermediate Compound G, (5$\alpha$)-3$\beta$-[3,3-di(3'-carboxy-5'-chloro-4'-hydroxy)phenyl-1-propen-2-yl]cholestane and its Ammonium Salt Boron tribromide-dimethyl sulfide complex (1M solution in methylene chloride, 3.4 mL) was added dropwise to a stirred solution of the diester, Compound F, (0.177 g, 0.219 mmol) in dichloroethane (12 mL) and the mixture was stirred at 60° C. for 24 hours. It was cooled in ice, quenched in water (5 mL), and stirred for 1 hour. Ethyl acetate was added to dissolve a precipitation and the organic layer was separated. The aqueous layer was extracted with chloroform (1×5 mL). The combined organic extracts were washed with water, dried (sodium sulfate) and evaporated to dryness. The solid residue was flash chromatographed on silica gel (15 g). Elution with chloroform-THF-97% formic acid (150:30:0.5) yielded a pure 3$\beta$ diastereoisomer, 97 mg (59.5%). An analytical sample was prepared by crystallization from methylene chloride-acetone mixture: mp 278° C.; IR (KBr) 3500–2600, 2927, 2856, 1668, 1607, 1447, 1232, 1181, 714 cm$^{-1}$; $^1$H NMR (acetone-d$_6$, 500 MHz) $\delta$7.71 (d, J=2.0 Hz, 1H), 7.675 (d, J=2.0 Hz, 1H), 7,575 (d, J=2.0 Hz, 1H), 7.47 (d, J=2.0 Hz, 1H), 6.2 (t, J=7.6 Hz, 1H), 0.92 (d, J=6.5 Hz, 3H), 0.85 (dd, J=6.5; 2.0 Hz, 6H), 0.75 (s, 3H), 0.69 (s, 3H); FABMS m/e (relative intensity) 683 (MH$^{+1}$, 20), 735 (MH$^+$-H$_2$O, 51); Anal. Calcd for C$_{44}$H$_{58}$Cl$_2$O$_6$×3/2 H$_2$O: C, 67.68; H, 7.87. Found: C, 67.46; H, 7.84.

The ammonium salt represented by Formula VIII was prepared by dissolving the diacid in ammonia and evaporation of the solution in vacuo. The ammonium salt showed mp 156° C. The compound of Formula VIII was subjected to anti-HIV testing as defined above. The following results were obtained.

| Run | IC$_{50}$ (Molar) | EC$_{50}$ (Molar) | TI$_{50}$ (IC/EC) |
|---|---|---|---|
| 1 | >3.20 × 10$^{-4}$ | 2.20 × 10$^{-5}$ | >1.50 × 10$^{+1}$ |
| 2 | >3.20 × 10$^{-4}$ | 2.20 × 10$^{-5}$ | >1.40 × 10$^{+1}$ |
| 3 | >3.20 × 10$^{-4}$ | 4.60 × 10$^{-5}$ | >6.90 × 10$^0$ |
| 4 | >3.20 × 10$^{-4}$ | 3.30 × 10$^{-5}$ | >9.60 × 10$^0$ |

Example 6

This Example illustrates the preparation and anti-HIV activity as indicated by the NCI anti-HIV screen shown above for (5$\alpha$-17-[5,5-di(3-ammoniumcarboxy-5-chloro-4-hydroxy)phenyl-1-methyl-4-pentenyl)androstane Formula IX.

Synthesis of Intermediate Compound A, Tosylhydrazone of methyl 3-metolithocholate P-toluenesulfonic hydrazide (3.05 g, 16.38 mmol) was added to a stirred solution of methyl 3-ketolithocholate, (3.18 g, 8.184 mmol) in acetic acid (50 mL). The mixture was stirred at room temperature for 20 hours, diluted with water (100 mL) with ice cooling. The precipitated white product was filtered off, washed with water, and crystallized from methanol-methylene chloride mixture. Yield 3.84 g, 84.3%: mp 184°–185° C.; IR (KBr) 3442, 3218, 2938, 2866, 1715, 1446, 1380, 1166 cm$^{-1}$; $^1$H NMR (CDCl$_3$, 200 MHz) $\delta$7.84 (d, J=8.2 Hz, 2H), 7.31 (d, J=8.2 HZ, 2H), 7.07 (s, 1H), 3.66 (s, 3H), 2.43 (s, 3H), 0.93 (s, 3H), 0,895 (d, J=6.2 Hz, 3H), 0.64 (s, 3H); FABMS m/e (relative intensity) 557 (MH$^+$, 100 ) 402 ( 68 ); Anal. Calcd for C$_{32}$H$_{48}$N$_2$O$_4$: C, 66.85; H, 8.77; N, 487. Found: C, 67.05; H, 8.74; N, 4.86.

Synthesis of Intermediate Compound B, Methyl cholanate

A solution of the tosylhydrazone, Compound A, (1.023 g, 1.837 mmol), sodium cyanoborohydride (577 mg, 9.185 mmol), and p-toluenesulfonic acid (100 mg) in DMF-sulfolane (10 mL, 1:1) was heated with stirring for 3 hours at 110° C. The reaction mixture was cooled in the ice-bath, quenched with brine (10 mL), extracted with ether (3×10 mL) and backwashed with brine (4×20 mL). The organic extract was dried (sodium sulfate), evaporated to dryness and the residue was flash chromatographed on silica gel (80 g). Elution with hexane-ethyl acetate (9:1) afforded the product, 0.484 g (70.4%) as an oil that crystallized on standing. An analytical sample was prepared by crystallization from hexane-ethyl acetate (6:1): mp 87° C.; IR (KBr) 2928, 2858, 1736, 1444, 1377, 1209, 1172 cm$^{-1}$; $^1$H NMR (CDCl$_3$, 200 MHz) $\delta$3.64 (s, 3H), 2.27 (m, 2H), 0.895 (d, J=6.4 Hz, 3H), 0.89 (s, 3H), 0.62 (s, 3H); CIMS m/e (relative intensity) 375 (MH$^+$, 100);

Synthesis of Intermediate Compound C, (5$\beta$)-17-(4-hydroxy -1-methylbutyl)androstane A solution of the ester, Compound B, (1.649 g, 4.402 mmol) in dry THF (12 mL) was added dropwise to 1M solution of LAH in ether (5.8 mL) and the mixture was stirred at 0° C. for 1 hour. The reaction mixture was quenched with water(0.22 mL), 15% sodium hydroxide (0.22 mL), and water (0.66 mL), diluted with methylene chloride (2 mL), filtered, and a precipitate on the filter was washed with methylene chloride. The filtrate was evaporated to dryness to afford alcohol, Compound C, as a white solid (1,259 g, 82.5%): mp 130° C.; IR (KBr) 3354, 2929, 2860, 1446, 1377, 1052, cm$^{-1}$; $^1$H NMR (CDCl$_3$, 200 MHz) $\delta$3.61 (m, 2H), 0.92 (d, J=5.5 Hz, 3H), 0.91 (s, 3H), 0.64 (s, 3H); CIMS m/e (relative intensity) 346 (M$^+$, 61), 329 (MH$^+$-H$_2$O, 100); Anal. Calcd for C$_{24}$H$_{42}$O: C, 83.17; H, 12.21. Found: C, 82.84; H, 12.55.

Synthesis of Intermediate Compound D, (5$\beta$)-17-(4-bromo-1- methylbutyl)androstane A solution of triphenylphosphine (1.427 g, 544 mmol) in dry methylene chloride (7 mL) was added dropwise with stirring to the solution of the alcohol, Compound C, (1.257 g, 3.63 mmol) and carbon tetrabromide (1.503 g, 4.538 mmol) in dry methylene chloride (12 mL) at 0°

C. The mixture was stirred at an ice bath for 10 minutes, solvent was removed in vacuo and the residue was stirred with ether (5×6 mL). The combined organic extracts were filtered, evaporated in vacuo and flash chromatographed on silica gel (45 g) to afford the product (1.257 g, 85%). An analytical sample was obtained by crystallization from acetone: mp 85° C.; IR (KBr) 2928, 2858, 1447, 1377, 1007 cm$^{-1}$; $^1$H NMR (CDCl$_3$, 200 MHz) δ3.38 (m, 2H), 0.92 (d, J=4.2 Hz, 3H), 0.91 (s, 3H), 0.64 (s, 3H); CIMS m/e (relative intensity) 408 (M+, 69), 407 (M+-H, 100), 329 (M+-Br, 67) Anal Calcd for C$_{24}$H$_{41}$Br: C, 70,41; H, 10,09. Found: C, 70,07; H, 10.43.

Synthesis of Intermediate Compound E,
(5β)-17-(1-methyl-4-triphenylphosphoniumbutyl)androstanyl bromide A solution of triphenylphosphine (8.55 mg, 33.26 mmol) and bromide, Compound D, (1,335 g, 3.26 mmol) in chlorobenzene (3 mL) was heated at 140° C. for 48 hours. The solvent was removed in vacuo and the residue was triturated with hexane. The phosphonium salt was filtered, washed with hexane, and dried in vacuum desiccator: mp 173°–175° C.; FABMS 591 (M+, 84); Anal Calcd for C$_{42}$H$_{56}$BrP: C, 75.09; H, 840. Found: C, 74.97; H, 8.57.

Synthesis of Intermediate Compound F,
(5β)-17-[5,5-di(3-chloro-4-methoxy-5-methoxycarbonyl)phenyl-1-methyl-4-pentenyl]androstane A solution of the phosphonium salt, Compound E, (1.567 g, 2.33 mmol) in dry THF (30 mL) was treated with sodium bis(trimethylsilyl)amide (1M solution, 2.33 mL) for 30 minutes at 0° C. A solution of the ketone, di(3-chloro-4-methoxy-5-methoxycarbonyl)phenyl ketone, (0.996 g, 2.33 mmol) in dry THF (5 mL) was added dropwise and the mixture was stirred at room temperature for 48 hours. It was quenched with a solution of ammonium chloride (300 mg) in water (10 mL). The organic layer was separated and the aqueous one extracted with ether (1×5 mL). The combined organic extracts were washed with brine (2×20 mL), dried (sodium sulfate) and the solvent was evaporated in vacuo to afford 2.5 g of a semisolid, which was flash chromatographed on silica gel (120 g). Elution with hexane-ethyl acetate (6:1) yielded an alkene, Compound F, as a glass, which failed to crystallize (1.370 g, 75.6%): IR (KBr) 2932, 2860, 1736, 1597, 1477, 1438, 1264, 1207, 1094, 1001 cm$^{-1}$; $^1$H NMR (CDCl$_3$, 500 MHz) δ7.495 (dd, J=2.4 Hz; 0.7, 1H), 7.48 (dd, J=2.2; 1.4 Hz, 1H), 7.33 (dd, J=2.2; 0.7 Hz, 1H), 727 (dd, J=2.3; 0.8 Hz, 1H), 6.07 (t, J=7.7 Hz, 1H), 4.00 (s, 3H), 3.39 (s, 3H), 3.92 (s, 3H), 3.91 (s, 3H), 0.91 (s, 3H), 0.84 (d, J=6.5 Hz, 3H), 0.625 (s, 3H); FABMS m/e (relative intensity) 739 (MH+, 19), 707 (MH+-MEOH, 52); Anal. Calcd for C$_{43}$H$_{56}$Cl$_2$O$_6$: C, 69.81; H, 7.63. Found C, 70.15; H, 7.81.

Synthesis of Compound G,
(5β)-17-[5,5-di(3-carboxy-5-chloro-4-hydroxy)phenyl-1-methyl-4-pentyl]androstane and its Ammonium Salt Boron tribromide dimethyl sulfide complex (1M solution in methylene chloride, 13.56 mL) was added dropwise to a stirred solution of the diester, Compound F, (1,318 g, 1,694 mmol) in dichloroethane (25 mL) and the mixture was stirred at 70° C. for 24 hours and at room temperature overnight. It was cooled in ice, quenched with water (10 mL), and stirred for 1 hour. The organic layer was separate and the aqueous one extracted with ethyl acetate (3×20 mL). The combined organic extracts were washed with water, dried (sodium sulfate) and evaporated to dryness. The solid residue (1.4 g) was flash chromatographed on silica gel (52 g). Elution with chloroform-THF-97% formic acid (150:30:0.5) yielded pure diacid, Compound G, 1.066 g (87.5%). An analytical sample was prepared by crystallization from methylene chloride-acetone mixture: mp 262°–263° C.; IR (KBr) 3500–2600, 2930, 2861, 1668, 1607, 1446, 1231, 1177, 711 cm$^{-1}$; $^1$H NMR (acetone-d$_6$, 500 MHz) δ7.70 (d, J=2.1 Hz, 1H), 7.675 (d, J=2.3 Hz, 1H), 7.56 (d, J=2.3 Hz, 1H), 7.49 (d, J=2.1 Hz, 1H), 6.18 (t, J=7.8 Hz, 1H 0.915 (s, 3H), 0.855 (d, J=6.6 Hz, 3H), 0.65 (s, 3H); FABMS m/e (relative intensity) 683 (MH+, 4 ); HR MS. Calcd: 683.2906. Found: 683.2895.

The ammonium salt represented by Formula IX was prepared by dissolving the diacid in ammonia and evaporation of the solution in vacuo. The compound of Formula IX was subjected to anti-HIV testing as defined above. The following results were obtained.

| Run | IC$_{50}$ (Molar) | EC$_{50}$ (Molar) | TI$_{50}$ (IC/EC) |
|---|---|---|---|
| 1 | >5.90 × 10$^{-5}$ | 4.10 × 10$^{-5}$ | >1.50 × 10$^0$ |
| 2 | >6.90 × 10$^{-5}$ | 1.90 × 10$^{-5}$ | 3.70 × 10$^0$ |
| 3 | 7.90 × 10$^{-5}$ | 2.00 × 10$^{-5}$ | 4.00 × 10$^0$ |

Example 7

This Example illustrates the preparation and anti-HIV activity as indicated by the NCI anti-HIV screen shown above for (5β)-3,3-difluoro-17-[5,5-di(3-ammoniumcarboxy-5-chloro-4-hydroxy)phenyl-1-methyl-4-pentenyl]androstane, Formula X.

Synthesis of Intermediate Compound A, Methyl 3,3-difluorocholanate

DAST (2.7 mL, 20.43 mmol) was added dropwise to a stirred solution of methyl 3-ketolithocholate (4.33 g, 11.14 mmol) in dry benzene (35 mL) at room temperature under argon atmosphere and the solution was stirred for 48 hours. It was cooled in the ice-bath, quenched with ice, followed with 0.63M sodium bicarbonate (10 mL). The benzene layer was separated and the aqueous layer extracted with benzene (1×10 mL). The combined organic extracts were dried (sodium sulfate) and evaporated to dryness. The solid residue was flash chromatographed on silica gel (200 g). Elution with hexane-ethyl acetate (6:1) yielded the difluoro derivative, Compound A, (4.46 g (97.5%)); an analytical sample was prepared by crystallization from hexane-ethyl acetate (6:1):mp 11°–112° C.; IR (KBr) 2936, 2887, 2867, 1740, 1453, 1373, 1216, 1178, 1108, 1079, 1025, 955 cm$^{-1}$; $^1$H NMR (CDCl$_3$, 200 MHz) δ3.67 (s, 3H), 0.97 (s, 3H), 0.91 (d, J=6.2 Hz, 3H), 0.65 (s, 3H); CIMS m/e (relative intensity) 411 (MH+, 100), 391 (MH+-HF, 25), 371 (MH+-2×HF); Anal. Calcd for C$_{25}$H$_{40}$F$_2$O$_2$:C, 73.13; H, 9.82. Found: C, 73.40; H, 10.10.

Synthesis of Intermediate Compound B,
(5β)-3,3-Difluoro-17-(1-hydroxypentyl-4)androstane A solution of the ester, Compound A, (189 mg, 0.419 mmol) in dry THF (1 mL) was added dropwise to 1M solution of LAH in ether (0.55 mL) and the mixture was stirred at 0° C. for 1 hour. The reaction mixture was quenched with water (1 drop), 15% sodium hydroxide (1 drop), and water (3 drops), diluted with methylene chloride (2 mL), filtered, and a precipitate on the filter was washed with methylene chloride. The filtrate was evaporated to dryness and obtained oil was flash chromatographed on silica gel (10 g). Elution with hexane-ethyl acetate (3:1) afforded the alcohol, Compound B, as a crystallizing oil, 152 mg (86.3%): mp 100° C.; IR (KBr) 3377, 2936, 2867, 1451, 1370, 1275, 1181, 1056, 1026, 955 cm$^{-1}$; $^1$H NMR (CDCl$_3$, 200 MHz) $\delta$3.62 (t, J=5.9 Hz, 2H), 0.97 (s, 3H), 0.925 (d, J=6.4 Hz, 3H), 0.66 (s, 3H); CIMS m/e (relative intensity) 382 (MH$^+$, 26), 365 (MH$^{30}$-H$_2$O, 46), 363 (MH$^{30}$ -HF, 48), 343 (MH$^+$-2×HF, 100); Anal. Calcd for C$_{24}$H$_{40}$F$_2$O: C, 75.35; H, 10.54. Found: C, 75.56; H, 10.84.

Synthesis of Intermediate Compound C, (5$\beta$)-3,3-Difluoro-17-(1-bromopentyl-4)androstane A solution of triphenylphosphine (573 mg, 2.185 mmol) in dry methylene chloride (2 mL) was added dropwise with stirring to the solution of the alcohol, Compound B, (557 mg, 1.456 mmol) and carbon tetrabromide (603.6 mg, 1.82 mmol) in dry methylene chloride (10 mL) at 0° C. The mixture was stirred at ice bath for 10 minutes, solvent was removed in vacuo and the residue was stirred with ether (4 ×5 mL). The combined organic extracts were filtered, evaporated in vacuo and flash chromatographed on silica gel (50 g). Yield 87.7%: mp 90° C. (acetone); IR (KBr) 2933, 2873, 1445, 1369, 1261, 1102, 956 cm$^{-1}$; $^1$H NMR (CDCl$_3$, 200 MHz) $\delta$3.39 (m, 2H), 0.97 (s, 3H), 0,925 (d, J=6.5 Hz, 3H), 0.66 (s, 3H); CIMS m/e (relative intensity) 444 (MH$^+$, 52), 425 (M$^+$-F, 100), 407, 405 (M$^+$-F-HF, 28), 365 (M$^+$-Br, 34); Anal. Calcd for C$_{24}$H$_{39}$F$_2$Br: C, 64.71; H, 8.82; F, 8.53. Found: C, 64.64; H, 8.91; F, 8.28.

Synthesis of Intermediate Compound D, (5$\beta$)-3,3-Difluoro-17-(4-pentyl)-androstanyltriphenylphosphonium bromide A solution of triphenylphosphine (288.7 mg, 1.101 mmol) and bromide, Compound C, (491.5 mg, 1,101 mmol) in chlorobenzene (1.5 mL) was heated at 140° C. for 48 hours. The solvent was removed in vacuo and the residue was triturated with hexane. The phosphonium salt was filtered, washed with hexane, and dried in vacuum desiccator: mp 135°–137° C.; $^1$H NMR (CD$_4$OD, 200 MHz) $\delta$7.9–7.7 (m, 15H), 3.4 (m, 2H), 0.98 (s, 3H), 0.84 (d, J=6.2 Hz, 3H), 0.66 (s, 3H); FABMS m/e (relative intensity) 627 (M$^+$, 92), 607 (M$^+$-HF, 55).

Synthesis of Intermediate E

A solution of the phosphonium salt, Compound D, (581 mg, 0,820 mmol) in dry THF (12 mL) was treated with sodium bis(trimethylsilyl)amide (1M solution, 0.82 mL) for 30 minutes at 0° C. A solution of the ketone, di(5-chloro-4-methoxy-3-methoxycarbonyl)phenyl ketone, (350 mg, 0.82 mmol) in dry THF (5 mL) was added dropwise and the mixture was stirred at room temperature for 48 hours. Usual work-up afforded 0.87 g of an oil which was flash-chromatographed on silica gel (45 g). Elution with hexane-ethyl acetate (6:1) yielded an alkene, 5$\beta$-3,3-difluoro-17-[5,5-di(3-methoxycarbonyl-5-chloro-4-methoxy)phenyl-1-methyl-4-pentyl]androstane, as a glass which failed to crystallize, 0,472 g (74%); IR (KBr) 2938, 2868, 1735, 1477, 1438, 1367, 1265, 1208, 1095, 1000 cm$^{-1}$; $^1$H NMR (CDCl$_3$, 200 MHz) 67 7.47 (d, J=2.3 Hz, 1H), 7.46 (d, J=2.1 Hz, 1H), 7.305 (d, J=2.1 Hz, 1H), 7.27 (d, J=2.3 Hz, 1H), 6.04 (t, J=7.7 Hz, 1H), 3.98 (s, 3H), 3.91 (s, 3H), 3.89 (s, 6H), 0.94 (s, 3H), 0.815 (d, J=6.3 Hz, 3h), 0.61 (s, 3H); FABMS m/e (relative intensity) 775 (MH$^+$, 26), 725 (M$^+$-HF, 29); Anal. Calcd for C$_{43}$H$_{54}$Cl$_2$F$_2$: C, 66.57; H, 7.02. Found: C, 66.58; H, 7.16.

Synthesis of the Compound having Formula X

Boron tribromide-dimethyl sulfide complex (1M solution in methylene chloride, 4.3 mL) was added dropwise to a stirred solution of the diester, 5$\beta$-3,3-difluoro-17-[5,5-di(3-methoxycarbonyl-5-chloro-4-methoxy)phenyl-1-methyl-4-pentyl]androstane, (410 mg, 0.529 mmol) in dichloroethane (8 mL) and the mixture was stirred at 70° C. for 28 hours and at room temperature overnight. It was cooled in ice, quenched with water (10 mL), stirred for 1 hour followed by extraction with ethyl acetate (3×15 mL). The combined organic extracts were washed with water, dried (sodium sulfate) and evaporated to dryness. The solid residue was flash chromatographed on silica gel (30 g). Elution with chloroform-THF-97% formic acid (150:30:0.5) yielded pure diacid 8, 370 mg. An analytical sample was prepared by crystallization from methylene chloride-acetone mixture: mp 180°–182° C.; IR (KBr) 3400–2600, 2933, 2866, 1669, 1607, 1444, 1232, 1178 cm$^{-1}$; $^1$H NMR (acetone-d$_6$, 200 MHz) $\delta$7.725 (d, J=1.9 Hz, 1H), 7.70 (d, J=2.2 Hz, 1H), 7.57 (d, J=2.2 Hz, 1H), 7.505 (d, J=1.9 Hz, 1H), 6.20 (t, J=7.6 Hz, 1H), 0.99 (m, 3H), 0.875 (d, J=6.3 Hz, 3H), 0.69 (s, 3H); FABMS m/e (relative intensity) 761 (MH$^+$ +H$_2$O+Na, 6).

The ammonium salt represented by formula X was prepared by dissolving the diacid in ammonia and evaporation of the solution in vacuo. The compound of formula X was subjected to anti-HIV testing as defined above. The following results were obtained.

| Run- | IC$_{50}$ (Molar) | EC$_{50}$ (Molar) | TI$_{50}$ (IC/EC) |
| --- | --- | --- | --- |
| 1 | 4.10 × 10$^{-5}$ | 2.40 × 10$^{-5}$ | 1.80 × 10$^0$ |

Example 8

This Example illustrates the preparation and anti-HIV activity as indicated by the NCI anti-HIV screen shown above for 1,1-di(3'-ammoniumcarboxy-5'-chloro-4'hydroxy) phenyl-1-untriacontene, Formula XI.

Synthesis of Di(3-carboxy-5-chloro-4-hydroxy)phenyl-1-buten-3-yl]-untriacontene and its Ammonium Salt Boron tribromide (1M solution in methylene chloride, 2.47 mL) was cooled in a dry ice-acetone bath and a solution of 1,1-(di(5'-chloro-2'-methoxy-3'methoxycarbonyl)phenyl]-1-untriacontene (247 mg, 0.296 mmol) in dry methylene chloride (6 mL) was added via septum in an argon atmosphere with magnetic stirring. The cooling bath was removed after 1 hour and stirring continued in an ambient temperature for two days. Reaction was quenched with water (3 mL), stirring continued for 30 minutes, and the product extracted with 10% NaHCO$_3$ (3×3 mL). The alkaline solution was washed with methylene chloride, acidified on cooling with concentrated HCl and the product extracted with ethyl acetate (3×3 mL). The organic extracts were washed with brine, dried (sodium sulfate) and concentrated in vacuo to afford a solid (150 mg, 65.4%): mp 173°–174° C. (chloroform-acetone); IR (KBr) 3500–2600, 2919, 2851, 1672, 1604, 1468, 1236, 1181, 900, 798, 720 cm$^{-1}$;

1H NMR (acetone-d$_6$, 200 MHz) δ7.695 (d, J=3 Hz, 1H), 7.67 (d, J=2.2 Hz, 1H), 7.565 (d, J=2.2 Hz, 1H), 7.48 (d, J=2 Hz, 1H), 6.18 (t, J=7.4 Hz, 1H), 2.13 (m, 2H), 1.49 (m, 2H), 1.27 (m, 54H), 0.86 (t, J=6.4 Hz, 3H); FABMS m/e (relative intensity) 797 (MNa$^+$, 7), 774 (M$^+$,11); Anal, Calcd for C$_{45}$H$_{68}$Cl$_2$O$_6$×2H$_2$O: C, 66.57; H, 8.94. Found: C, 66.80; H, 8.99.

The ammonium salt represented by formula XI was prepared by dissolving the diacid in ammonia and evaporation of the solution in vacuo. The ammonium salt showed mp 190° C. The compound of Formula XI was subjected to anti-HIV testing as defined above. The following results were obtained.

| Run | IC$_{50}$ (Molar) | EC$_{50}$ (Molar) | TI$_{50}$ (IC/EC) |
| --- | --- | --- | --- |
| 1 | >2.22 × 10$^{-4}$ | 1.33 × 10$^{-5}$ | >1.67 × 10$^{+1}$ |
| 2 | >2.22 × 10$^{-4}$ | 1.63 × 10$^{-5}$ | >1.36 × 10$^{+4}$ |
| 3 | >2.20 × 10$^{-4}$ | 1.10 × 10$^{-5}$ | >1.90 × 10$^{+1}$ |
| 4 | >2.20 × 10$^{-4}$ | 9.30 × 10$^{-6}$ | >2.40 × 10$^{+1}$ |

Example 9

This Example illustrates the preparation and anti-HIV activity as indicated by the NCI anti-HIV screen shown above for 1,1-di(5'-bromo-3'-carbomethoxy-4'-methoxy)phenyl-1-heptene, Formula XII.

Synthesis of Intermediate Compound A, Di(5-bromo-3-carboxmethoxy-4-methoxy)phenylmethane 3-Bromomethylenedisalicyclic acid (8,179 g, 18.34 mmol) was partially dissolved in acetone (250 mL), potassium carbonate (20.09 g) was added followed by dimethyl sulfate (9.5 mL) and the mixture was heated at reflux with stirring for 24 hours. Acetone was removed in vacuo, water (100 mL) was added and the mixture was extracted with methylene chloride (6×30 mL). The combined organic extracts were washed with 2% potassium hydroxide (50 mL), brine, dried (sodium sulfate) and evaporated to dryness. The residue was crystallized from chloroform-hexane mixture, yield 7.75 g (84.2%: mp 107°-108° C.; IR (KBr) 2948, 1725, 1595, 1553, 1472, 1433, 1314, 1251, 1202, 1089, 996, 926, 876, 827, 800, 717 cm$^{-1}$; $^1$H NMR (CDCl$_3$, 200 MHz) d 7.55 (d, J=2.2 Hz, 2H), 7.50 (d, J=2.2 Hz, 2H), 3.92 (s, 6H), 3.91 (s, 6H), 3.88 (s, 2H); CIMS m/e (relative intensity) 503 (MH$^{+1}$, 76), 471 (100, 257 (63; Anal. Calcd for C$_{19}$H$_{18}$Br$_2$O$_6$: C, 45.44; H, 3.61. Found: C, 45.73; H, 3.81.1

Synthesis of Intermediate Compound B, Di(5-bromo-3-carbomethoxy-4-methoxy)phenylketone Diphenylmethane, Compound A, (6.02 g) was partially dissolved in acetic anhydride (110 mL), the solution was cooled in ice bath and chromium trioxide (5.05 g) was added in small portions with stirring. The mixture was stirred at ambient temperature for 3 hours and 5 minutes at reflux and was filtered after cooling. The filtrated mixture of chromium salts and the ketone, Compound B, was washed thoroughly with chloroform and then was stirred twice with chloroform (2×80 mL). The solvents were removed in vacuo and the residue was crystallized from chloroform-hexane mixture, yield 4.84 g; mp 130°-131 ° C.; IR (KBr) 2954, 1742, 1657, 1589, 1472, 1438, 1318, 1268, 1201, 1090, 986 cm$^{-1}$; $^1$H NMR (CDCl$_3$, 200 MHz) d 8.16 (d, J =2.2 Hz, 2H, 8.12 (d, J=2.2 Hz, 2H, 4.03 (s, 6H), 3.95 (s, 6H) ; CIMS m/e (relative intensity) 517 (MH$^+$, 100), 485 (25); Anal. Calcd for C$_{19}$H$_{16}$Br$_2$O$_7$: C, 44.19; H, 3.10. Found: C, 43.87; H, 3.02.

Synthesis of 1,1-Di(5-bromo-4-methoxy-3-methoxycarbonyl) phenyl-1-heptene, the Compound of Formula XII N-hexyltriphenylphosphonium bromide (1.43 g, 3,346 mmol) was suspended in dry THF (25 mL), the mixture was cooled in ice-bath and sodium bis(trimethylsilyl)amide (1M solution in THF, 3.35 mL) was added dropwise. The mixture was stirred for 20 minutes, a solution of the bromoketone, Compound B, (1.554 g, 3.01 mmol) in THF (12 mL) was added dropwise. The ice-bath was removed, the reaction mixture was stirred 1 hour at 60° C. and 20 hours at ambient temperature. Reaction was quenched with ammonium chloride solution, THF phase was separate and aqueous one extracted with ether. The combined organic extracts were dried (sodium sulfate), evaporated to dryness followed by flash chromatography on silica gel (hexane-ethyl acetate 4:1) to yield 1,593 g of crystalline product (91%): mp 52°-53°C. (ethanol); IR (KBr) 2946, 2860, 1732, 1472, 1435, 1288, 1250, 1209, 1086, 997, 726 cm$^{-1}$; $^1$H NMR (CDCl$_3$, 200 MHz) d 7.53 (d, J=2.2 Hz, 2H), 7.495 (d, J=2.2 Hz, 1H), 7.48 (d, J=2.2 Hz, 1H), 6.06 (t, J=7.6 Hz, 1H), 3.99 (s, 3h), 3.92 (s, 6h), 3.915 (s, 3h), 2.08 (m, 2H), 1.45 (m, 2H), 1.26 (m, 4H), 0.88 (t, J=6.7 Hz, 3H); CIMS m/e (relative intensity) (585, MH$^+$, 85), 553 (100); Anal. Calcd for C$_{25}$H$_{28}$Br$_2$O$_6$: C, 51.39; H, 4.83. Found C, 51.41; H, 5.00.

The compound of formula XII was subjected to anti-HIV testing as defined above. The following results were obtained.

| Run | IC$_{50}$ (Molar) | EC$_{50}$ (Molar) | TI$_{50}$ (IC/EC) |
| --- | --- | --- | --- |
| 1 | >8.95 × 10$^{-6}$ | 4.97 × 10$^{-5}$ | >1.80 × 10$^0$ |
| 2 | >8.95 × 10$^{-6}$ | 4.86 × 10$^{-6}$ | >1.84 × 10$^0$ |
| 3 | >8.95 × 10$^{-6}$ | 2.47 × 10$^{-6}$ | >3.62 × 10$^0$ |
| 4 | >8.95 × 10$^{-6}$ | 2.72 × 10$^{-7}$ | >3.29 × 10$^{+1}$ |

Example 10

This Example illustrates the preparation and anti-HIV activity as indicated by the NCI anti-HIV screen shown above for 1,1-di(3'-ammoniumcarboxy-5'-chloro-4'-hydroxy)phenyl-1-undecene, Formula XIII.

Synthesis of the Compound of Formula XIII

Boron tribromide (1M solution in methylene chloride, 1.75 mL) was cooled in a dry ice-acetone bath and a solution of 1,1[di(5'-chloro-2'-methoxy-3'methoxycarbonyl)phenyl]-1-undecene (181 mg, 0.328 mmol) in dry methylene chloride (3 mL) was added via septum in an argon atmosphere with magnetic stirring. The cooling bath was removed after 1 hour and stirring continued in an ambient temperature for 16 hours. Reaction was quenched with water (3 mL), stirring continued for 30 minutes, and a product extracted with 10% KOH (3×3 mL). The alkaline solution was washed with methylene chloride, acidified on cooling with concentrated HCl (1.2 mL) and the product extracted with ethyl acetate (3×3 mL). The organic extracts were washed with brine, dried (sodium sulfate) and concentrated in vacuo to afford an oil (93 mg, 57%), which crystallized on trituration with methylene chloride, mp 207° C.: IR (KBr) 3500-2500, 2925, 2855, 1665, 1445, 1232, 1117, 899, 799, 719 cm$^{-1}$; FABMS m/e (relative intensity) 494 (M$^+$, 18), 477 (MH$^+$-H$_2$O, 20); $^1$H NMR (CDCl$_3$, 200 MHz) δ7.60 (bs, 2H), 7.42 (bs, 1H), 7.34 (bs, 1H), 6.06 (t, 1H), 2.08 (m, 2H), 1.46 (m, 2H), 1.25 (m, 12H), 0.88 (t, 3H); Anal. Calcd for C$_{25}$H$_{28}$Cl$_2$O$_6$: C, 60.61; H, 5.70. Found: C, 60.47; H, 6.10.

The ammonium salt represented by formula XIII was prepared by dissolving the diacid in ammonia and evaporation of the solution in vacuo. The ammonium salt showed mp 153°–155° C. Formula XIII was subjected to anti-HIV testing as defined above. The following results were obtained.

| Run | IC$_{50}$ (Molar) | EC$_{50}$ (Molar) | TI$_{50}$ (IC/EC) |
| --- | --- | --- | --- |
| 1 | >4.91 × 10$^{-5}$ | 3.73 × 10$^{-5}$ | >1.32 × 10$^0$ |

Example 11

This Example illustrates the preparation and anti-HIV activity as indicated by the NCI anti-HIV screen shown above for 1,1-di(3'-ammoniumcarboxy-5'-chloro-4'-hydroxy)phenyl-1-heptadecene, Formula XIV.

Synthesis of the Compound of Formula XIV

Boron tribromide (1M solution in methylene chloride, 1.6 mL) was cooled in a dry ice-acetone bath and a solution of 1,1-[di(5'-chloro-2'-methoxy-3'methoxycarbonyl)phenyl]-1-heptadecene (190.3 mg, 0.30 mmol) in dry methylene chloride (3 mL) was added via septum in an argon atmosphere with magnetic stirring. The cooling bath was removed after 1.5 hours and stirring continued in an ambient temperature for 16 hours. More of BBr$_3$ solution (0.9 mL) was added and the reaction was continued overnight. The reaction mixture was quenched with water (3 mL), stirred for 30 minutes and the product was extracted with 10% KOH (3×3 mL). The alkaline solution was washed with methylene chloride, acidified on cooling with concentrated HCl (1.2 mL) and the product extracted with ethyl acetate (3×3 mL). The organic extracts were washed with brine, dried (sodium sulfate) and concentrated in vacuo to afford a solid (166 mg, 95.6%), mp 207° C. (methylene chloride): IR (KBr) 3500–2500, 2918, 2863, 1665, 1448, 1228, 1179 cm$^{-1}$; FABMS m/e (relative intensity) 578 (M$^+$, 9), 561 (10); Anal. Calcd for C$_{32}$H$_{40}$Cl$_2$O$_6$: C, 64.24; H, 6.96. Found: C, 64.23; H, 7.30.

The ammonium salt represented by formula XIV was prepared by dissolving the diacid in ammonia and evaporation of the solution in vacuo. The compound of formula XIV was subjected to anti-HIV testing as defined above. The following results were obtained.

| Run | IC$_{50}$ (Molar) | EC$_{50}$ (Molar) | TI$_{50}$ (IC/EC) |
| --- | --- | --- | --- |
| 3 | >3.50 × 10$^{-5}$ | 4.62 × 10$^{-6}$ | >7.57 × 10$^0$ |

Example 12

This Example illustrates the preparation and anti-HIV activity as indicated by the NCI anti-HIV screen shown above for 1,1-[di(3'-carbomethoxy-5'bromo-2'-hydroxy)phenyl-1-heptene, Formula XV.

Synthesis of the Compound of Formula XV

Boron tribromide (1M solution in methylene chloride, 1.0 mL) was cooled in a dry ice-acetone bath and a solution for 1,1[di(5'-bromo-2'-methoxy-3'methoxycarbonyl)phenyl]-1-heptene (109 mg, 0.187 mmol) in dry methylene chloride (2.5 mL) was added via septum in an argon atmosphere with magnetic stirring. The cooling bath was removed after 1 hour and stirring continued in an ambient temperature for two days. Reaction was quenched with water (3 mL), stirring continued for 30 minutes and a product extracted with 10% KOH (3×3 mL). The alkaline solution was washed with methylene chloride, acidified on cooling with concentrated HCl (1.2 mL) and the product extracted with ethyl acetate (3×3 mL). The organic extracts were washed with brine, dried (sodium sulfate) and concentrated in vacuo to afford a solid (70 mg, 71%), mp 214° C. (methylene chloride): IR KBr) 3350–2800 3444, 2938, 1674, 1443, 1285, 1057 cm$^{-1}$; Anal. Calcd for C$_{21}$H$_{20}$Br$_2$O$_6$×3/2 H$_2$O: C, 45.43; H, 4.18. Found: C, 45.63; H, 3.94.

The ammonium salt represented by formula XV was prepared by dissolving the diacid in ammonia and evaporation of the solution in vacuo. The ammonium salt showed mp 209°–211° C. The compound of formula XV was subjected to anti-HIV testing as defined above. The following results were obtained.

| Run | IC$_{50}$ (Molar) | EC$_{50}$ (Molar) | TI$_{50}$ (IC/EC) |
| --- | --- | --- | --- |
| 1 | >2.18 × 10$^{-5}$ | 1.53 × 10$^{-5}$ | >1.43 × 10$^0$ |

Example 13

This Example illustrates the preparation and anti-HIV activity as indicated by the NCI anti-HIV screen shown above for 1,1-di(3'-carbamoyl-5'-chloro-4'-methoxy)phenyl-1-heptene, Formula XVI.

Synthesis of the Compound of Formula XVI

Dimethyl ester, di(3'-carbomethoxy-5'-chloro-4-methoxy)phenyl-1-heptene, was hydrolyzed with aqueous-methanolic potassium hydroxide and the obtained diacid, di(3'-carboxy-5'-chloro-4-methoxy)phenyl-1-heptene, (112 mg) was suspended in dry benzene (2 mL), oxalyl chloride (0.4 mL) was added and the mixture was refluxed for 15 minutes. The obtained solution was stirred for 2 hours and the solvent was removed in vacuo. The acid chloride was dissolved in dry benzene (4 mL) and sodium dried ammonia was passed through the stirred solution for 2 hours. Water was added, followed by chloroform and the mixture was filtered from contaminating oxalyl amide. The organic phase was washed with 5% solution of potassium hydroxide, the brine, dried (sodium sulfate) and evaporated to dryness. The residue was purified by preparative TLC on silica gel (ethyl acetate-ethanol, 3) and the amide (60 mg) was crystallized from methylene chloride-hexane mixture, mp 61°–62° C.; IR (KBr) 3447, 3263, 2930, 2855, 1718, 1687, 1579, 1474, 1375, 1250, 991 cm$^{-1}$; $^1$H NMR (acetone-d$_6$, 200 MHz) δ7.66 (d, J =1.9 Hz, 2H), 7.52 (d, J=2Hz, 1H), 7.43 (d, J=1.9 Hz, 1H), 6.32 (m, 1H), 3.99 (s, 3H), 3.98 (s, 3H), 2.13 (m, 2H), 1.51 (m, 2H), 1.29 (m, 4H), 0.87 (t, J=5.5 Hz, 3H) ; FABMS m/e (relative intensity) 465 (MH$^+$, 16), 448 (100); Anal. Calcd for C$_{23}$H$_{26}$Cl$_2$N$_2$O$_4$×H$_2$O: C, 57.14; H, 5.83. Found: C, 57.09; H, 5.72.

The compound of formula XVI was subjected to anti-HIV testing as defined above. The following results were obtained.

| Run | IC$_{50}$ (Molar) | EC$_{50}$ (Molar) | TI$_{50}$ (IC/EC) |
|---|---|---|---|
| 1 | 1.74 × 10$^{-5}$ | 1 × 10$^{-4}$ | 9.07 × 10$^0$ |
| 2 | 1.72 × 10$^{-5}$ | 4.27 × 10$^{-5}$ | 1.10 × 10$^{+1}$ |
| 3 | 1.63 × 10$^{-5}$ | 5.62 × 10$^{-5}$ | 1.08 × 10$^{+1}$ |
| 4 | 1.34 × 10$^{-5}$ | 2.46 × 10$^{-6}$ | 5.47 × 10$^0$ |

Example 14

This Example illustrates the preparation and anti-HIV activity as indicated by the NCI anti-HIV screen shown above for 4-bromo-1,1-di(3'-ammoniumcarboxy-5'-chloro-4'-methoxy)phenyl-1-butene, Formula XVII.

Synthesis of the Compound of Formula XVII

Boron tribromide (1M solution in methylene chloride, 2.61 mL) was cooled in a dry ice-acetone bath and a solution of 4-bromo-1,1-[di(5'-chloro-2'-methoxy-3'-methoxycarbonyl)-phenyl]-2-butene (181 mg, 0.328 mmol) in dry methylene chloride (3 mL) was added via septum in an argon atmosphere with magnetic stirring. The cooling bath was removed after 1 hour and stirring continued in an ambient temperature for 2 days. Reaction was quenched with water (3 mL), stirring continued for 30 minutes and a product extracted with 10% KOH (3×3 mL). The alkaline solution was washed with methylene chloride, acidified on cooling with concentrated HCl (1.2 mL) and the product extracted with ethyl acetate (3×3 mL). The organic extracts were washed with brine, dried (sodium sulfate) and concentrated in vacuo to afford a solid (120 mg, 77%): mp 258°–259° C. (acetone-methylene chloride); IR (KBr) 3500–2500, 3075, 1668, 1606, 1440, 1360, 1299, 1234, 1174, 798, 711 cm$^{-1}$; $^1$H NMR (acetone-d$_6$, 200 MHz) δ7.75 (d, J=2.1 Hz, 1H), 7.74 (d, J=2.2 Hz, 1H), 7.60 (d, J=2.2 Hz, 1H), 7.56 (d, J=2.1 Hz, 1H), 6.22 (t, J=7.2 Hz, 1H), 3.64 (t, J=6.7 Hz, 2H), 2.78 (m, 2H); Anal. Calcd for C$_{18}$H$_{13}$BrCl$_2$O$_6$: C, 45.41; H, 2.75. Found: C, 45.23; H, 2.86.

The ammonium salt represented by formula XVII was prepared by dissolving the diacid in ammonia and evaporation of the solution in vacuo. The compound of formula XVII was subjected to anti-HIV testing as defined above. The following results were obtained.

| Run | IC$_{50}$ (Molar) | EC$_{50}$ (Molar) | TI$_{50}$ (IC/EC) |
|---|---|---|---|
| 1 | 2.14 × 10$^{-4}$ | 1.36 × 10$^{-4}$ | 1.58 × 10$^0$ |
| 2 | 2.37 × 10$^{-4}$ | 1.22 × 10$^{-4}$ | 1.93 × 10$^0$ |
| 3 | 1.81 × 10$^{-4}$ | 1.21 × 10$^{-4}$ | 1.50 × 10$^0$ |
| 4 | 2.58 × 10$^{-4}$ | 9.51 × 10$^{-5}$ | 2.71 × 10$^0$ |

Example 15

This Example illustrates the preparation and anti-HIV activity as indicated by the NCI anti-HIV screen shown above for 1,1-di(3'-ammoniumcarboxy-4'-hydroxy)phenyl-1-decane, Formula XVIII.

Synthesis of the Compound of Formula XVIII 1,1-Di(5-bromo-3-carboxy-4-hydroxy)phenyl-1-undecene (52 mg, 0.089 mmol) was hydrogenated for two days in mixture of methanol (6 mL) and freshly distilled triethylamine (3 mL) in the presence of 10% Pd/C (30 mg) at ambient temperature and 60 psi initial pressure. The catalyst was filtered off, washed with methanol, the solvent removed in vacuo and diluted NaOH (1M, 1 mL) was added. The mixture was extracted with ethyl ether (3×3 mL), the aqueous phase was acidified with 1M HCl and extracted with ethyl acetate (3×3 mL). The combined extracts were washed twice with brine, dried (sodium sulfate) and concentrated in vacuo to yield 32 mg of solid (83%) which was crystallized from methylene chloride-hexane mixture: mp 143° C.; IR (KBr) 360–2600, 2925, 2854, 1664, 1614, 1489, 1444, 1293, 1205, 891, 717 cm$^{-1}$; $^1$H NMR (acetone-d$_6$, 200 MHz) δ7.83 (d, J=2.3 Hz, 2H), 7.50 (dd, J=2.2; 8.6 Hz, 2H), 6.90 (d, J=8.6 Hz, 2H), 4.00 (m, 1H), 1.26 (m, 20H), 0.87 (t, J=6.5 Hz, 3H); FABMS m/e (relative intensity) 429 (MH$^+$, 53), 411 (45); Anal. Calcd for C$_{25}$H$_{32}$O$_6$: C, 70.07; H, 7.53. Found: C, 70.43; H, 7.90.

The ammonium salt represented by formula XVIII was prepared by dissolving the diacid in ammonia and evaporation of the solution in vacuo. The compound of formula XVIII was subjected to anti-HIV testing as defined above. The following results were obtained.

| Run | IC$_{50}$ (Molar) | EC$_{50}$ (Molar) | TI$_{50}$ (IC/EC) |
|---|---|---|---|
| 1 | 8.46 × 10$^{-5}$ | 3.32 × 10$^{-5}$ | 2.55 × 10$^0$ |

Example 16

This Example illustrates the preparation and anti-HIV activity as indicated by the NCI anti-HIV screen shown above for 4-bromo-1,1-di(3'-carbomethoxy-5'-chloro4'-methoxy)phenyl-1-butene, Formula XIX.

Synthesis of Intermediate Compound A, 3-t-butyldimethylsilyloxypropyltriphenylphosphonium bromide 3-Bromo-tert-butyldimethylsilyl-1-propanol ( 2.7 g, 10.75 mmole) and triphenylphosphine (2.83 g, 10.75 mmole) were dissolved in hot acetonitrile (3 mL) and heated under reflux for 30 hours. The reaction mixture was left to cool, the solvent removed in vacuo and oily residue triturated with hexane until crystallization came to completion. The white salt was filtered on the next day, washed with hexane (3×5 mL), and in a vacuum desiccator. Yield 4.995 g (93%), mp 137°–139° C.; $^1$H NMR (DMSO-d$_6$, 200 MHz) d 7.9–7.8 (m, 15H), 3.68 (t, J=5.9 Hz, 2H), 3.53 (m, 2H), 1.67 (m, 2H), 0.84 ( s, 9H), 0.02 (s, 6H), EIMS 435 (M$^+$-Br).

Synthesis of Intermediate Compound B, 1,1-Di(5-chloro-4-methoxy-3-methoxycarbonyl)-phenyl-4-t-butyldimethylsilyloxy-1-butene Compound A (1.27 g, 2.46 mmol) was suspended in dry DME (10 mL) and n-butyl lithium (2.4M, 1.03 mL) was added dropwise. A solution of the di(5-chloro-4-methoxy-3-methoxycarbonyl)phenyl ketone, (1.05 g, 2.46 mmol) in DME (12 mL) was added dropwise to the solution of the ylide and the mixture was stirred at 63° C. for 22 hours. The cooled reaction mixture was quenched with aqueous ammonium chloride solution (250 mg in 10 mL of water). The aqueous layer was extracted with ether (5 mL) and the combined organic extracts were washed with brine and dried (sodium sulfate). The solvent was evaporated in vacuo to afford 2.05 g of an oil, which was flash chromatographed on silica gel (90 g, hexane-ethyl acetate 1) to yield a colorless oil which crystallized (0,617 g); mp 40° C. (ethanol): IR(KBr) 2946, 2861, 1735, 1596, 1475, 1436, 1252, 1210, 1096, 1001, 842, 777 cm$^{-1}$; $^1$H NMR (CDCl$_3$, 200 MHz)

d 7.50 (d, J=2.2 Hz, 1H), 7.46 (d, J =2.0 Hz, 1H), 7.373 (d, J=2.0 Hz, 1H), 7.273 (d, J=2.2 Hz, 1H), 6.09 (t, J=7.5 Hz, 1H), 3.97 (s, 3H), 3.91 (s, 3H), 3.89 (s, 6H), 3.68 (t, J=6.4 Hz, 2H), 2.30 (m, 2H), 0.87 (s, 9H), 0.025 (s, 6H); FABMS m/e (relative intensity) 583 (MH+, 63), 551 (90), 525 (100); Anal. Calcd for $C_{28}H_{36}Cl_2O_7Si$: C, 57.62; H, 6.22. Found: C, 57.80; H, 6.30.

Synthesis of Intermediate Compound C, 1,1-Di(5-chloro-4-methoxy-3-methoxycarbonyl)phenyl-4-hydroxy-1-butene The silyl ether, 1,1-di(5-chloro-4-methoxy-3-methoxycarbonyl)phenyl-4-tert-dimethylsilyloxy-1-butene, (407 mg, 0.697 mmol) was stirred in THF solution (4 mL) with tetra-n-butylammonium fluoride (1M solution in THF, 1.4 mL) at 0° C. for 2.5 hours. The solvent was removed in vacuo, brine added, a product was extracted with benzene. The combined extracts were washed with brine, dried (sodium sulfate), evaporated in vacuo and flash chromatographed on silica gel to yield a colorless oil, 0.255 g: IR(neat) 3528, 3061, 2952, 2875, 2832, 1732, 1596, 1477, 1437, 1402, 1359, 1269, 1210, 1168, 1094, 999, 739 cm$^{-1}$; $^1$H NMR (CDCl$_3$, 200 MHz) d 7.525 (d, J=2.5 Hz, 1H), 7.515 (d, J=2.2 Hz, 1H), 7.38 (d, J=2.2 Hz, 1H), 7.32 (d, J=2.5 Hz, 1H), 6.14 (5, J=7.5 Hz, 1H), 4.00 (s, 3H), 3.935 (s, 3H), 3.923 (s, 3H), 3,915 (s, 3H), 3.75 (m, 2H), 2.39 (m, 2H); CIMS m/e (relative intensity) 469 (MH+, 100), 451 (35), 437 (780; Anal. Calcd for $C_{22}H_{22}Cl_2O_7$: C, 56.30; H, 4.73. Found: C, 56.65; H, 4.86.

Synthesis of the Compound of Formula XIX

A solution of the alcohol, Compound C, (215 mg, 0.458 mmol) and carbon tetrabromide (304 mg, 0.916 mmol) in dry acetonitrile (3 mL) was heated under reflux with stirring and a solution of triphenylphosphine (360 mg, 1.374) was added dropwise over 2 minutes. The mixture was heated under reflux for 2 hours, cooled, the solvent was removed in vacuo and the residue was extracted with benzene (3×5 mL). The combined extracts were filtered and the solvent was removed in vacuo. The residue was flash chromatographed on silica gel (20 g, hexane-ethyl acetate 4:1) to the bromide (0.20 g, 82%), mp 68° C. (ethanol):IR(KBr) 2949, 1730, 1476, 1437, 1297, 1254, 1214, 995 cm$^{-1}$; $^1$H NMR (CDCl$_3$, 200 MHz) d 7.51 (m, 2H), 7.36 (d, J=2.1 Hz, 1H), 7.33 (d, J=2.3 Hz, 1H), 6.08 (5, J=7.2 Hz, 1H), 4.00 (s, 3H), 3.93 (s, 9H), 3.46 (t, J=6.6 Hz, 2H), 2.69 (q, J=6.7 Hz, 2H); CIMS m/e (relative intensity) 533 (MH+, 94), 501 (100); Anal. Calcd for $C_{22}H_{21}BrCl_2O_6$: C, 49.65; H, 3.98. Found: C, 49.29; H, 4.00.

The compound of formula XIX was subjected to anti-HIV testing as defined above. The following results were obtained.

| Run | IC$_{50}$ (Molar) | EC$_{50}$ (Molar) | TI$_{50}$ (IC/EC) |
| --- | --- | --- | --- |
| 1 | 2.15 × 10$^{-5}$ | 8.19 × 10$^{-6}$ | 2.62 × 10$^0$ |
| 2 | 1.52 × 10$^{-5}$ | 7.73 × 10$^{-6}$ | 1.96 × 10$^0$ |

Example 17

This Example illustrates the preparation and anti-HIV activity as indicated by the NCI anti-HIV screen shown above for 1,1-di(3'-ammoniumcarboxy-5'-bromo-4'-hydroxy)phenyl-1-undecene, Formula XX.

Synthesis of the Compound of Formula XX 1,1-Di(5'-bromo-3'-carbomethoxy-4'-methoxy)phenyl-1-undecene (0.567 mmol) and sodium iodide (0,680 g) were stirred in dry acetonitrile (4 mL) in argon atmosphere. Trimethylsilyl chloride (1.44 mL, 11.34 mmol, 20 eq) was added dropwise at room temperature and reaction mixture was stirred under reflux for 48 hours. The reaction mixture was quenched with water (3 mL) and 3M HCl (0.3 mL) and extracted with ethyl acetate (4×3 mL). The combined extracts were washed with brine, 10% sodium sulfite (10 mL) and 5% sodium bicarbonate (3×4 mL). The basic extracts were acidified with concentrated hydrochloric acid and product was extracted with ethyl acetate (4×5 mL). The organic extracts were washed with brine, dried (sodium sulfate) to yield a solid (141 rag): mp 226°-227° C. (methylene chloride-acetone); IR (KBr) 3350-2600, 2924, 2854, 1663, 1605, 1442, 1230, 1177, 712 cm$^1$; $^1$H NMR (acetone-d$_6$, 200 MHz) δ7.73 (m,3H) , 7.65 (d, J=2 Hz, 1H), 6.19 (t, 7.5 Hz, 1H), 2.15 (m, 2H), 1.5 (m, 2H, 1.26 (m, 12H), 0.87 (t, J=6.6 Hz, 3H); FABMS m/e (relative intensity) 584 (MH+, 21), 567 (13), 460 (29); Anal. Calcd for $C_{25}H_{28}Br_2O_6$: C, 51.39; H, 4.83. Found: C, 51.15; H, 5.12.

The ammonium salt represented by formula XX was prepared by dissolving the diacid in ammonia and evaporation of the solution in vacuo. The compound of formula XX was subjected to anti-HIV testing as defined above. The following results were obtained.

| Run | IC$_{50}$ (Molar) | EC$_{50}$ (Molar) | TI$_{50}$ (IC/EC) |
| --- | --- | --- | --- |
| 1 | >1.91 × 10$^{-4}$ | 5.55 × 10$^{-5}$ | >3.44 × 10$^0$ |

Example 18

This Example illustrates the preparation and anti-HIV activity as indicated by the NCI anti-HIV screen shown above for 1,1-[di(3'-ammoniumcarboxy-5'-bromo-2'-methoxy)phenyl-1-heptene, Formula XXI.

Synthesis of the Compound of Formula XXI 1,1-[Di(5'-bromo-2'-methoxy-3'-methoxycarbonyl)-phenyl-1-heptene (1 mmol) was suspended in aqueous methanol (1:10, v/v, 2 ml ). A solution of potassium hydroxide (200 mg) in methanol (1 ml) was added and the mixture refluxed with magnetic stirring until starting ester disappeared (4 hours). The solvent was removed in vacuo, water added and a solution was acidified with diluted hydrochloric acid (1M, 1 mL). The product was extracted with ethyl acetate (3×2 mL) and the combined extracts were washed twice with brine. The organic extract was dried (sodium sulfate) and evaporated in vacuo to yield a diacid, 73.5%, mp 144°-146° C. (benzene-hexane): Ir (KBr) 3500-2600, 3429, 3076, 2930, 2858, 1699, 1572, 1461, 1419, 1290, 1237, 1002 cm$^{-1}$; $^1$H NMR (200 MHz, Acetone-d$_6$) δ7.89 (d, J=2.6 Hz, 1H), 7.81 (d, J=2.6 Hz, 1H), 7.68 (d, J=2.6 Hz, 1H), 7.64 (d, J=2.6 Hz, 1H), 6.19 (t, J=7.3 Hz, 1H), 3.61 (s, 3H), 3.57 (s, 3H), 2.17 (m, 2H), 1.53 (m, 2H), 1.32 (m, 4H), 0.87 (t, J=6.8 Hz, 3H) ; FABMS m/e (relative intensity) 557 (MH+, 4), 539(47); Anal Calcd for $C_{23}H_{24}Br_2O_6$: C, 49.66; H, 4.35. Found: C, 49.46; H, 4.54.

The ammonium salt represented by formula XXI was prepared by dissolving the diacid in ammonia and evaporation of the solution in vacuo. The ammonium salt showed mp 103°–106° C. The compound of Formula XXI was subjected to anti-HIV testing as defined above. The following results were obtained.

| Run | IC$_{50}$ (Molar) | EC$_{50}$ (Molar) | TI$_{50}$ (IC/EC) |
|---|---|---|---|
| 1 | 1.75 × 10$^{-4}$ | 9.71 × 10$^{-5}$ | 1.80 × 10$^0$ |
| 2 | 2.44 × 10$^{-4}$ | 6.93 × 10$^{-5}$ | 3.52 × 10$^0$ |

Example 19

This Example illustrates the preparation and anti-HIV activity as indicated by the NCI anti-HIV screen shown above for 1,1-[di(3'-ammoniumcarboxy-4'-hydroxy) phenyl-1-heptadecane, Formula XXII.

Synthesis of
1,1-di(3'-carboxy-4'hydroxylphenyltheptadecane and diammonium salt, Formula XXII.

1,1-di(3'-carboxy-5'-chloro-4'-hydroxy)phenyl-1-heptadecene (46 mg. 0.0794 mmole) was hydrogenated for two days in a mixture of methanol (2mL) and freshly distilled triethylamine (1 ml) in the presence of 10% Pd/C (21 mg) at ambient temperature and normal pressure. The catalyst was filtered off, washed with methanol, the solvent removed in vacuo and diluted NaOH (1M, 1 mL) was added. The mixture was extracted with ethyl ether (3×3 mL), the aqueous phase was acidified with 1M HCl and extracted with ethyl acetate (3x3 mL). The combined extracts were washed twice with brine, dried (sodium sulfate) and concentrated in vacuo to yield 38 mg of solid (83 %), mp 133° C. (methylene chloridehexane): JR(KBr) 3600–2600, 2922, 2852, 1665, 1612, 1445, 1293, 1204, 891, 717; $^1$H NMR (acetone-d$_6$, 200 MHz) δ7.82 (d, J =2.3 Hz, 2H), 7.50 (dd, J=2.3 Hz; 8.6 Hz, 2H), 6.90 (d, J=8.6 Hz, 2H), 3.97 (m, 1H), 1.27 (m, 30H), 0.88 (t, J=6.5 Hz, 3H); FABMS m/e (relative intensity ) 511 (MH+, 4), 495 (18); Anal Calcd for C$_{31}$H$_{42}$O$_6$×3/2 H$_2$O; C, 69.24; H, 8.44. Found: C, 68.97; H, 8.69.

The ammonium salt represented by formula XXII was prepared by dissolving the diacid in ammonia and evaporation of the solution in vacuo, mp 193° C. The compound of Formula XXII was subjected to anti-HIV testing as defined above. The following results were obtained.

| Run | IC$_{50}$ (Molar) | EC$_{50}$ (Molar) | TI$_{50}$ (IC/EC) |
|---|---|---|---|
| 1 | 5.14 × 10$^{-5}$ | 3.29 × 10$^{-5}$ | 1.56 × 10$^0$ |
| 2 | 1.19 × 10$^{-4}$ | 3.90 × 10$^{-6}$ | 3.06 × 10$^{+1}$ |
| 4 | 5.14 × 10$^{-5}$ | 3.29 × 10$^{-6}$ | 1.56 × 10$^0$ |
| 5 | 1.19 × 10$^{-4}$ | 3.90 × 10$^{-6}$ | 3.05 × 10$^{+1}$ |

Example 20

This Example illustrates the preparation and anti-HIV activity as indicated by the NCI anti-HIV screen shown above for 1,1-[di-(3'-ammoniumcarboxy-5'-bromo-2'methoxy)phenyl]-1-undecene, Formula XXIII.

Synthesis of Intermediate Compound A

Sodium hydride (79.6 mg, 1.99 mmol, 60% dispersion in mineral oil) was washed with n-hexane (3×2 mL). Dimethyl sulfoxide (2 mL) was introduced via a syringe and the mixture was heated at 75° C. until the evolution of hydrogen ceased. The clear solution was cooled in an ice-water bath and a solution of the n-decylphosphonium bromide (874 mg, 1.99 mmol) in DMSO (4 mL) was added dropwise. The resulting solution was stirred at room temperature for 15 minutes. A solution of the bromobenzophenone, 5,5'dibromo-2,2'-dimethoxy-3,3'dicarbomethoxybenzophenone, (642 mg, 1.24 mmol) in warm DMSO (5 mL) was added dropwise and the reaction mixture heated at 55° C. for 22 hours. It was cooled in an ice-water bath. A solution of ammonium chloride (200 mg) in water (5 mL) was added and the reaction mixture was extracted with ethyl ether (5×5 mL). The organic extracts were washed twice with brine, dried over sodium sulfate, and evaporated in vacuo. A flash chromatography on silica gel (230–400 mesh), elution with n-hexane/ethyl acetate, 4:1, yielded decene, 1,1-[di(5'-bromo-2'-methoxy-3'-methoxycarbonyl) phenyl]-1-undecene, (466 mg, 64%) as an oil: IR (KBr) 3072, 2925, 2853, 1736, 1570, 1436, 1285, 1253, 1195, 1164, 1149, 1006 cm$^{-1}$; $^1$H NMR (CDCl$_3$, 200 MHz) δ7.88 (d, J=2.5 Hz, 1H), 7.79 (d, J =2.5 Hz, 1H), 7.55 (d, J=2.5 Hz, 1H), 7.50 (d, J=2.5 Hz, 1H), 6.07 (t, J=7.3 Hz, 1H), 3.88 (s, 3H), 3.87 (s, 3H), 3.52 (s, 3H), 3.49 (s, 3H), 2.09 (m, 2H), 1.26 (m, 14H), 0.88 (t, J=6.3 Hz, 3H); CIMS m/e (relative intensity) 641 (MH+, 4), 609 (MH$_+$-MeOH, 100).

Synthesis of the Compound of Formula XXIII

Bromo diester (1.37 mg, 0.214 mmol) was suspended in aqueous methanol (1:10, v/v, 24 ml). A solution of potassium hydroxide (52 mg) in methanol (1 mL) was added and the mixture refluxed with magnetic stirring until the starting ester disappeared (4 hours). The solvent was removed in vacuo, water added and a solution was acidified with diluted hydrochloric acid (1M, 1 ml). The product was extracted with chloroform (4×2 ml) and the combined extracts were washed with a brine. The organic extract was dried (sodium sulfate) and evaporated in vacuo to yield a diacid 1-44 (126 mg, 96%), mp 108° C. (ether-hexane): IR (KBr) 3500–2500, 2926, 2854, 1702, 1570, 1462, 1416, 1237, 1003 cm$^{-1}$; $^1$H NMR (200 MHz, acetone-d$_6$) δ7.89 (d, J=2.6 Hz, 1H), 7.81 (d, J - 2.6 Hz, 1H), 7.68 (d, J=2.6 Hz, 1H), 7.64 (d, J=2.6 Hz, 1H), 6.19 (t, J=7.3 Hz, 1H), 3,61 (s, 3H), 3.57 (s, 3H), 2.17 (m, 2H), 1.53 (m, 2H), 1.32 (m, 4H), 0.87 (t, J=6.8 Hz, 3 h) ; $^1$H NMR (200 MHz, acetone-d$_6$) δ7.865 (d, J=2.6 Hz, 1 h), 7.785 (d, J=2.6 Hz, 1 h), 7.66 (d, J=2.6 Hz, 1H), 7.61 (d, J=2.6 Hz, 1H), 6.17 (t, J=7.3 Hz, 1H), 3.59 (s, 3H), 3.55 (s, 3H), 2.17 (m, H), 1.53 (m, 2H), 1.26 (m, 12H), 0.87 (t, J=7 Hz, 3H); FABMS m/e (relative intensity) 657 (M$^+$+2Na, 27), 635 (MH$^+$+Na, 32), 595 (16); Anal. Calcd for C$_{27}$H$_{32}$Br$_2$O$_6$×H$_2$O: C, 51.44; H, 5.44. Found: C, 51.47; H, 5.19.

The ammonium salt represented by formula XXIII was prepared by dissolving the diacid in ammonia and evaporation of the solution in vacuo. The ammonium salt showed mp 190° C. The compound of Formula XXIII was subjected to anti-HIV testing as defined above. The following results were obtained. The results indicate that the compound is cytotoxic.

| Run | IC$_{50}$ (Molar) | EC$_{50}$ (Molar) | TI$_{50}$ (IC/EC) |
|---|---|---|---|
| 1 | 8.89 × 10$^{-5}$ | | |
| 2 | 7.95 × 10$^{-5}$ | | |
| 3 | 6.83 × 10$^{-5}$ | | |

| Run | IC$_{50}$ (Molar) | EC$_{50}$ (Molar) | TI$_{50}$ (IC/EC) |
|---|---|---|---|
| 4 | 6.98 × 10$^{-5}$ | | |

Example 21

This Example illustrates the preparation and anti-HIV activity as indicated by the NCI anti-HIV screen shown above for di(3'-carbomethoxy-5'-chloro-4'-methoxy)phenyl-1-heptene, Formula XXVI.

Synthesis of Intermediate Compound A, 1,1-Di(3-carboxy-5-chloro-4-hydroxy)phenylmethane This compound was prepared by a slight modification of the published procedure cited in Example 1. 3-Chlorosalicyclic acid (32.4 g, 0.187 mmol) was placed in a 1 L three-necked, round-bottomed flask equipped with a mechanical stirrer, a 500 mL pressure equalizing dropping funnel, and a thermometer. The solid was dissolved in methanol (140 mL), water (25 mL) was added, and the mixture was vigorously stirred at dry ice-acetone bath temperature while concentrated sulfuric acid (325 mL) was added at such a rate to keep temperature below 0° C. The reaction mixture was stirred on an ice bath for 1 hour and then cooled in a dry ice-acetone bath again. An aqueous solution of 37% formaldehyde (75 mL) was added at such a rate to keep the temperature below 0° C. The mixture was stirred at 0° C. for 4 hours and was left overnight at room temperature. It was poured on crushed ice (1.5 kg) and the precipitate was filtered and dried, first at room temperature overnight and then in a vacuum desiccator, to afford a solid (34.5 g). The product was recrystallized from chloroform-methanol (2:1): mp 296° C.

Synthesis of Intermediate Compound B, 1,1-Di(5-chloro-4-methoxy-3-methoxycarbonyl)-phenylmethane Compound A (1, 8.55 g, 23.95 mmol) was placed in a 500 mL three-necked, round-bottomed flask equipped with a mechanical stirrer, a 50 mL pressure equalizing dropping funnel, and a reflux condenser connected to a drying tube. The acid was dissolved in acetone (240 mL), Mallincrodt, AR), and ground anhydrous potassium carbonate (26.42 g, 191.2 mmol) was added, followed by dimethyl sulfate (16.31 g, 12.23 mL, 129 mmol). The reaction mixture was vigorously stirred under reflux for 2 days. The solvent was removed in vacuo and water (100 mL) was added, followed by methylene chloride (80 mL). The resulting mixture was filtered through a celite pad, the organic phase was separated, the residue on the filtration funnel was washed twice with methylene chloride (2×30 mL), and the second filtrate used for re-extraction of the aqueous phase. The combined organic extracts were washed with water, dried (sodium sulfate) and evaporated in vacuo to yield the product as a colorless solid, 9.24 g. The reaction was scaled up three times without loss of yield. It would be more convenient on scaling up to filter off the inorganic salts from the acetone solution before evaporation of the solvent. The crude product was dissolved in boiling methylene chloride, hexane was added until solution became turbid, and crystallization came to completion in the refrigerator, yielding pure product (8.2 g, 81%): mp 131°-132° C.; IR (KBr) 2975, 2925, 1730, 1600, 1560, 1480, 1435, 1320, 1280; 1250, 1205, 1095, 1000, 925, 835, 790, 725 cm$^{-1}$; $^{1}$H NMR (500 MHz, CDCl$_3$) d 7.50 (d, J=2.3 Hz, 2H), 7.32 (d, J=2.3, 2H), 3.92 (s, 12H), 3.87 (s, 2H); CIMS m/e (relative intensity) 413 (MH$^+$, 100), 381(71); Anal. Calcd for C$_{19}$H$_{18}$Cl$_2$O$_6$: C, 55.34; H, 4.37. Found: C, 55.08; H, 4.45.

Synthesis of Intermediate Compound C, 1,1-Di(5-chloro-4-methoxy-3-methoxycarbonyl)benzophenone Compound B (1, 24.99 g, 60.47 mmol) was placed in a 1000 mL one-necked, round-bottomed flask equipped with a Teflon-coated magnetic stirring bar and a reflux condenser connected to a drying tube. Compound A was partially dissolved in acetic anhydride (500 mL, Baker, AR). The mixture was cooled in an ice bath and chromic anhydride (24.26 g, 242.6 mmol) was added in small portions over 0.5 hours. The bath was removed and the mixture was stirred at room temperature for 2 hours and then heated under reflux for 1 minute and overnight at room temperature. The chromium salts were filtered off and washed with methylene chloride (5×20 mL). The solvent was removed in vacuo and the solidified residue was flash chromatographed on silica gel (300 g). On scaling up it is more convenient to crystallize first the crude reaction product from methylene chloride-hexane mixture and purify the mother liquors by chromatography. Elution with methylene chloride (2.5 L) afforded the benzophenone derivative, Compound C (18.78 g, 72.8%): mp 118°×119° C.; IR (KBr) 1744, 1662, 1476, 1269, 988 cm$^{-1}$; $^{1}$H NMR (500 MHz, CDCl$_3$) d 8.07 (d, J=2.3 Hz, 2H), 7.97 (d, J=2.3 Hz, 2H), 4.03 (s, 6H), 3.94 (s, 6H); CIMS m/e (relative intensity) 427 (M$^+$, 100), 381 (71); Anal. Calcd for C$_{19}$H$_{16}$Cl$_2$O$_6$: C, 53.52; H, 3.76. Found: C, 53.28; H, 3.73.

Synthesis of Intermediate Compound D, N-Hexyltriphenylphosphonium bromide

Compound D was prepared by modification of the procedure indicated in Example 1. N-Hexane was used in place of ether to purify the salt, m p 198°-198.5° C., yield 94%.

Synthesis of the Compound of Formula XXVI

Sodium hydride (54 mg, 1.35 mol, 60% dispersion in mineral oil) was washed with n-hexane (3×5 mL). Dimethyl sulfoxide (2 mL) was introduced via a syringe and the mixture was heated at 75° C. until the evolution of hydrogen ceased. The clear solution was cooled in an ice-water bath and a solution of the n-hexyltriphenylphosphonium bromide (576 mg, 1.35 mmol) in DMSO (3 mL) was added dropwise. The resulting solution was stirred at room temperature for 15 minutes. A solution of the ketone, Compound C, (0.86 mmol, 369 mg) in warm DMSO (6 mL) was added dropwise and the reaction mixture heated at 55° C. for 27 hours. It was cooled in an ice-water bath. A solution of ammonium chloride (143 mg) in water (5 ml) was added and the reaction mixture was extracted with ethyl ether (5×5 ml). The organic extracts were washed twice with brine, dried over sodium sulfate, and evaporated in vacuo. A flash chromatography on silica gel (230–400 mesh), elution with n-hexane/ethyl acetate, 4:1, yielded starting ketone (39 mg) and heptene 1-7 (320 mg, 75%), mp 88° C.: IR (KBr) 3046, 1732, 1595, 1364, 1250, 1211 cm$^{-1}$ $^{1}$H NMR (CDCl$_3$, 500 MHz) d 7.49 (d, J= 2.4 Hz, 1H), 7.48 (d, J=2.2 Hz, 1H), 7.32 (d, J=2.2 Hz, 1H), 7.30 (d, J=2.4 Hz, 1H), 6.07 (t, J=7.6 Hz, 1H), 4.00 (s, 3H), 3.93 (s, 3H), 3.92 (s, 3H), 3.91 (S, 3H), 2.08 (m, 2H), 1.44 (m, 2H), 1.27 (m, 4H), 0.88 (t, J=6.9 Hz, 3H) ; CIMS m/e (relative intensity): 495 (MH+, 100) 463 (12); Anal Calcd for $C_{25}H_{28}Cl_2O_6$; C, 60.61; H, 5.70. Found: C, 60.52; H, 5.76.

The compound of Formula XXVI was subjected to anti-HIV testing as defined above. The following results were obtained.

| Run | IC$_{50}$ (Molar) | EC$_{50}$ (Molar) | TI$_{50}$ (IC/EC) |
|---|---|---|---|
| 1 | >2.91 × 10$^{-5}$ | 2.08 × 10$^{-5}$ | >1.40 × 10$^0$ |
| 2 | >2.82 × 10$^{-5}$ | 1.72 × 10$^{-5}$ | >1.64 × 10$^0$ |
| 3 | >2.91 × 10$^{-5}$ | 1.01 × 10$^{-5}$ | >2.90 × 10$^0$ |

Example 22

This Example illustrates the preparation and anti-HIV activity as indicated by the NCI anti-HIV screen shown above for 1,1-[di(3'-ammoniumcarboxy-5'-chloro-4'-methoxy)phenyl-2-(pentafluorophenyl)ethene, Formula XXV.

Synthesis of the Compound of Formula XXV 1,1-di(3'-carboxy-5'-chloro-4'-methoxy) phenyl-2(pentafluorophenyl)ethene was obtained by saponification of the ester, 1,1-(di (3'-carbomethoxy-5'-chloro-4'-methoxy) phenyl-2-(pentafluorophenyl)ethene, yield 98.6% mp 227° C. (methylene chloride-acetone mixture): IR (KBr) 3434, 2941, 1704, 1654, 1598, 1560, 1482, 1421, 1299, 1257, 1198, 1104, 1043, 984, 927 cm$^{-1}$; $^1$H NMR (acetone-d$_6$, 200 MHz) δ7.77 (d, J=2.5 Hz, 1H), 7.68 (d, J=2 Hz, 1H), 7.53 (d, J=2Hz, 1H), 7.46 (d, J=2.5 Hz, 1H), 6.86 (s, 1H), 3.97 (s, 3H), 3.97 (s, 3H), 1.97 (m, 2H, H-2), 1.23 (m, 16H), 0.87 (t., J=6.2 Hz, H-11); Anal. Calcd for $C_{24}H_{13}Cl_2F_5O_6 \times (CH_3)_2CO$: C, 52.19; H, 2.57. Found: C, 52.47; H, 2.57.

The ammonium salt represented by formula XXV was prepared by dissolving the diacid in ammonia and evaporation of the solution in vacuo. The compound of Formula XXV was subjected to anti-HIV testing as defined above. The following results were obtained.

| Run | IC$_{50}$ (Molar) | EC$_{50}$ (Molar) | TI$_{50}$ (IC/EC) |
|---|---|---|---|
| 1 | 4.34 × 10$^{-4}$ | 1.40 × 10$^{-4}$ | 3.10 × 10$^0$ |
| 2 | 5.52 × 10$^{-4}$ | 1.02 × 10$^{-4}$ | 5.43 × 10$^0$ |
| 3 | 4.12 × 10$^{-4}$ | 1.76 × 10$^{-4}$ | 2.34 × 10$^0$ |

Example 23

This Example illustrates the preparation and anti-HIV activity as indicated by the NCI anti-HIV screen shown above for 1,1-di(3'-carboxy-5'-chloro-4'-methoxy)phenyl-1-heptadecene, Formula XXIV.

Synthesis of the Compound of Formula XXIV

The acid was obtained by saponification of the diester, di(3'-carbomethoxy-5'-chloro-4'-methoxy)phenyl-1-heptadecene. It was carried out as for ester, di-(3'-carbomethoxy-5'-chloro-4'-methoxy)phenyl-1-heptene in Example 21, yield 93 mg (99%). Recrystallization from a methylene chloride-hexane mixture afforded an analytical sample, mp 125°×126° C.: IR (KBr) 2933, 1682, 1478, 1285, 999, 719 cm$^{-1}$; EIMS m/e (relative intensity) 606 (M+, 100); Anal. Calcd for $C_{33}H_{44}Cl_2O_6$: C, 65.23; H, 7.30. Found: C, 64.90; H, 7.93.

Formula XXIV was subjected to anti-HIV testing as defined above. The following results were obtained. The results indicate that the compound is cytotoxic.

| Run | IC$_{50}$ (Molar) | EC$_{50}$ (Molar) | TI$_{50}$ (IC/EC) |
|---|---|---|---|
| 1 | 2.66 × 10$^{-5}$ | | |
| 2 | 2.59 × 10$^{-5}$ | | |

Example 24

This Example illustrates the preparation and anti-HIV activity as indicated by the NCI anti-HIV screen shown above for 1,1-di(3'-ammoniumcarboxy-5'-chloro-4'methoxy) phenyl-1-undecene, Formula XXVII.

Synthesis of the Compound of Formula XXVII

Methoxy acid was prepared by saponification of the diester di(3'-carbomethoxy-5'-chloro-4'-methoxy)phenyl-1-undecene, carried out as for ester of Example 21, yield 95 mg (98%). An analytical sample was prepared by recrystallization from methylene chloride, mp 155° C.: IR (KBr) 3500–2600, 3429, 2925, 2854, 1699, 1597, 1559, 1478, 1429, 1379, 1250, 1102, 100 cm$^{-1}$; EIMS m/e (relative intensity) 524(46), 522(87), 487(38), 477(48), 398(87), 396(100), 383(49), 350(87), 347(53), 333(30), 315(22), 306(23); Anal. Calcd for $C_{27}H_{32}Cl_2O_6 \times 3/2H_2O$: C, 58.91 H, 6.41. Found: C, 55.38; H, 6.12. The ammonium salt was obtained by dissolving the acid in concentrated ammonia, evaporating of the solvent and vacuum drying, mp 138° C.

The compound of Formula XXVII was subjected to anti-HIV testing as defined above. The following results were obtained.

| Run | IC$_{50}$ (Molar) | EC$_{50}$ (Molar) | TI$_{50}$ (IC/EC) |
|---|---|---|---|
| 1 | 1.49 × 10$^{-4}$ | 1.00 × 10$^{-4}$ | 1.48 × 10$^0$ |
| 2 | 1.66 × 10$^{-4}$ | 4.27 × 10$^{-5}$ | 3.89 × 10$^0$ |
| 3 | 1.69 × 10$^{-4}$ | 5.62 × 10$^{-5}$ | 3.01 × 10$^0$ |

Approximate values for 50% effective concentration (EC$_{50}$) (protection in infected cells), 50% inhibitory concentration (IC$_{50}$) and the therapeutic index (IC$_{50}$/EC$_{50}$) have been calculated for each test and are provided in the tables of each Example.

A comparison of these values appears to indicate that Compounds of Formulas IV, V, VI, XI and XII have the greatest effect on inhibiting HIV-infected cells, while having a lesser effect on uninfected cells.

Figure 5:
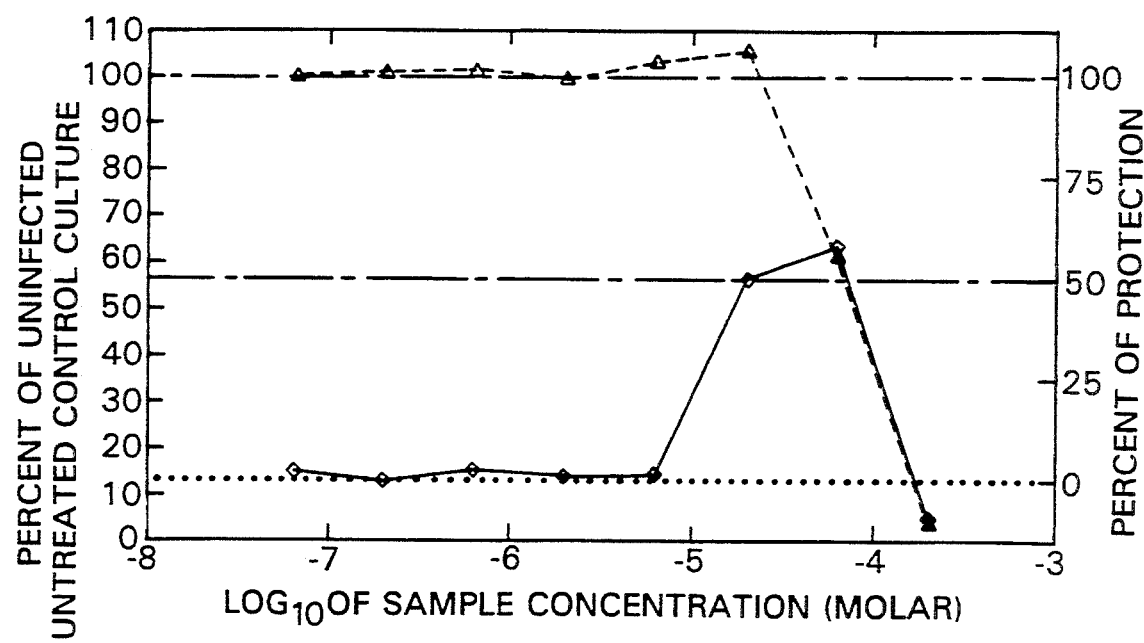
FIG. 5 depicts in vitro testing results for anti-HIV activity for the compound of Example 6 in accordance with the present invention.
Figure 6:
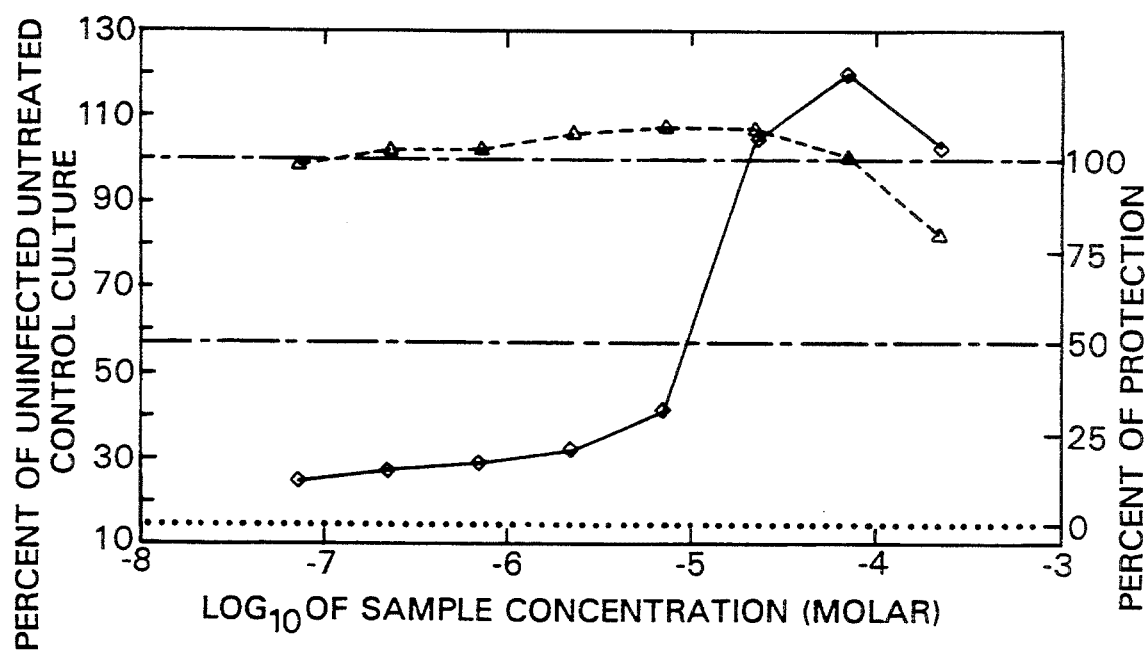
FIG. 6 depicts in vitro testing results for anti-HIV activity for the compound of Example 8 in accordance with the present invention.

FIGS. 1, 5 and 6 display a plot of the log$_{10}$ of the concentrations (as μg/mL or molar as shown), of the Examples 1, 6 and 8 compounds, respectively, against the measured test values expressed as a percentage of the uninfected, untreated control values. The solid line depicts the percentage of surviving HIV-infected cells treated with sample (at the indicated concentration) relative to uninfected, untreated controls. The solid line expresses the in vitro anti-HIV activity of the compound of the tested compound. The dashed line depicts the percentage of surviving uninfected cells treated with the compound of the Example relative to the same uninfected, untreated controls. The dashed line expresses the in vitro growth inhibitory properties of the compound of the Example. The viral cytopathic effect of a compound of each Example is indicated by a combination of dashes and dots. This reference line shows the extent of destruction of cells by the virus in the absence of treatment and is used as a quality control parameter. Survival values of this parameter less then 50% are considered acceptable in the current protocol.

As illustrated in FIGS. 1, 5 and 6 and the tables provided in each example, the compounds of the present invention are effective in inhibiting the growth of HIV-infected cells while leaving uninfected cells unharmed. The most effective compounds studied in terms of prevention of the cytopathic effect of HIV in CEM lymphocytes appear to be cosalane (structure IV) and the compound having structure XII, a compound of general Formula I. Therefor, compounds having the biphenyl ring attached to a six-membered ring of the steroid and compounds simply consisting of the biphenyl ring structure appear to have the greatest activity as anti-HIV agents because they do relatively low harm to uninfected cells while being highly effective against HIV-infected cells.

What is claimed:

1. A compound having the following structure:

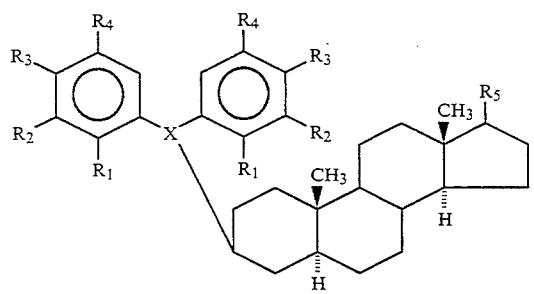

wherein $R_1$ and $R_5$ independently are H; a halogen; hydroxy; amino; lower alkoxy; benzoyloxy; lower acyloxy; COOH or a salt thereof; $SO_3H$ or a salt thereof; $PO_3H_2$ or a salt thereof; $C_8H_{17}$ or a longer chain alkyl; aryl group; COOR where R is aryl or lower alkyl; $SO_3R$ where R is aryl or lower alkyl; $PO_3(R)_2$ where R is aryl or lower alkyl; CONR'R" where R' and R" are each independently H, lower alkyl, aryl, or OH; $SO_2NR'R"$ where R' and R" are each independently H, lower alkyl, or aryl; SR where R is lower alkyl or aryl; $SCH_2Ph$; SCOR where R is lower alkyl or aryl; or NR'R" where R' and R" are each independently H, lower alkyl, or aryl; and X is an alkane or alkene radical having up to seven carbon atoms.

2. The compound of claim 1 wherein $R_2$ is chlorine and $R_4$ is $CO_2NH_4$.

3. A compound having the following structure:

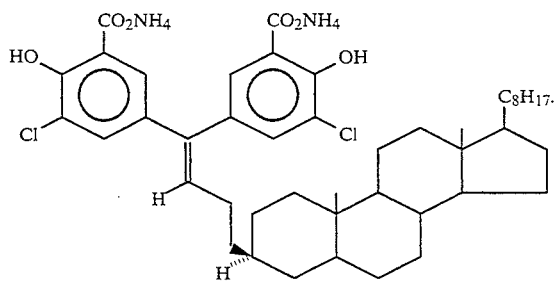

4. A compound having the following structure:

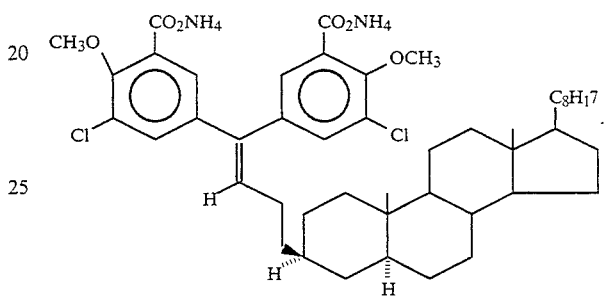

5. A compound having the following structure:

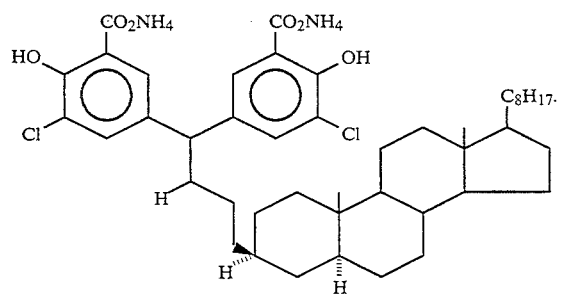

6. The compound of claim 1 having the following structure:

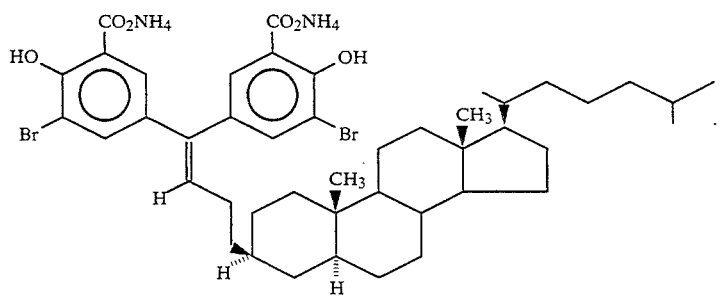

7. The compound of claim 1 having the following structure:

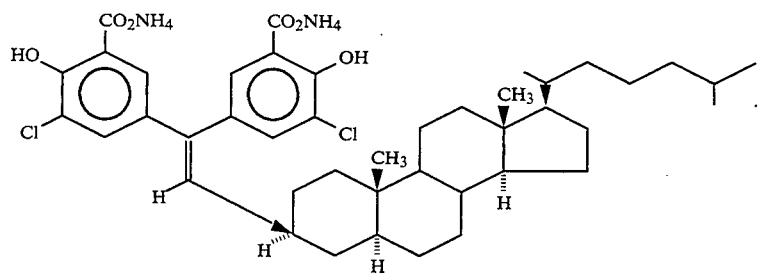

8. A pharmaceutical formulation comprising a therapeutically effective amount of a compound according to claim 1 and a pharmaceutically acceptable carrier therefor.

9. A pharmaceutical composition of matter, in unit dosage form, for use as an anti-HIV agent, said composition comprising:
 (i) an amount of a compound according to claim 1 sufficient to release a pharmacologically effective amount of said compound to the brain; and
 (ii) a pharmaceutically acceptable carrier therefor.

* * * * *